(12) United States Patent
Krieg

(10) Patent No.: US 7,736,646 B2
(45) Date of Patent: Jun. 15, 2010

(54) METHODS FOR MODULATING ANGIOGENESIS WITH APELIN COMPOSITIONS

(75) Inventor: Paul A. Krieg, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 797 days.

(21) Appl. No.: 10/799,417

(22) Filed: Mar. 12, 2004

(65) Prior Publication Data

US 2004/0219152 A1 Nov. 4, 2004

Related U.S. Application Data

(60) Provisional application No. 60/528,155, filed on Dec. 9, 2003, provisional application No. 60/454,034, filed on Mar. 12, 2003.

(51) Int. Cl.
*A61K 39/395* (2006.01)
(52) U.S. Cl. .................. 424/133.1; 424/146.1
(58) Field of Classification Search .............. 424/146.1, 424/133.1
See application file for complete search history.

(56) References Cited

U.S. PATENT DOCUMENTS

| | | | |
|---|---|---|---|
| 6,492,324 B1 | 12/2002 | Hinuma et al. ................. | 514/2 |
| 2003/0092618 A1 | 5/2003 | Hinuma et al. ................. | 514/12 |
| 2004/0033495 A1 | 2/2004 | Murray et al. ................. | 435/6 |
| 2006/0159676 A1* | 7/2006 | Krieg ...................... | 424/133.1 |
| 2010/0028256 A1* | 2/2010 | St. Croix et al. ........... | 424/1.49 |

FOREIGN PATENT DOCUMENTS

WO    WO00/68224    11/2000

OTHER PUBLICATIONS

Jain (Scientific American Jul. 1994).*
Chatterjee et al (Cancer Immunol. Imunother., 1994.*
Dermer (Biotechnology 12: 320, 1994).*
Gura et al (Science vol. 278 Nov. 1997 1041-1042).*
Traschel et al. (Adv. Drug Delivery Rev. 58:735-754 (2006)).*
Seaver (1994; Genetic Engineering vol. 14(14):pp. 10 and 21).*
Burgess et al, (Journal of Cell Biology 111:2129-2138 (1990)).*
Lazar et al (Molecular and Cellular Biology 8:1247-1252 (1988)).*
Schwartz et al, (Proc Natl Acad Sci USA 84:6408-6411 (1987)).*
Lin et al (Biochemistry USA 14:1559-1563 (1975)).*
Stein (Pharmacology and Therapeutics 85: 231-236 (2000).*
Stein (J. Clinical Investigation 108(5): 641-644 (2001).*
Caplen, Gene Therapy 11(16): 1241-1248 ( 2004).*
Chirila et al, Biomaterials 23:321-342 (2002).*
Gerwirtz et al., Blood 92(3): 712-736 (1998).*
Jen et al., Stem Cells 18: 307-319 (2000).*
Opalinska et al., Nature Reviews 1:503-514 (2002).*
Scherer et al., Nature Biotechnology 21(12), pp. 1457-1465 (2003).*
Kurreck et al., Current Opinion Drug Discovery and Development 7(2): 179-187 (2004).*
Lu et al., RNA Interference Technology, Cambridge, Appasani, ed., 2005, p. 303.*
Samarsky et al., RNA Interference Technology, Cambridge, Appasani, ed., 2005, pp. 389-394.*
Sioud, RNA Silencing, Methods and Protocols, Humana Press, 2005.*
Simeoni et al., RNA Silencing, Methods and Protocols, Humana Press, 2005, p. 251.*
Mahato et al., Expert Opinion on Drug Delivery, Jan. 2005, vol. 2, No. 1, pp. 3-28.*
Felmeden et al., Eur. Heart J. 24:586-603 (2003).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Kleinz et al. Regul. Peptides 118:119-125 (2004).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Lederman et al (Molecular Immunology 28:1171-1181, 1991).*
Li et al (Proc. Natl. Acad. Sci. USA 77:3211-3214, 1980).*
Cayabyab et al., 2000, "Apelin, the Natural Ligand of the Orphan Seven-Transmembrane Receptor APJ, Inhibits Human Immunodeficiency Virus Type 1 Entry," *Journal of Virology*, 7(24):11972-11976.
Devic et al., 1999, "Amino acid sequence and embryonic expression of *msr/apj*, the mouse homolog of Xenopus X-msr and human APJ," *Mechanisms of Development*, 84:199-203.
Devic et al., 1999, "Expression of Endothelial Precursors of a New Family of Receptors Sharing Similarities with CXC Chemokine Receptors," *Pathologie Biologie* 47(4):330-338.
Eyetech Study Group, 2003, "Anti-Vascular Endothelial Growth Factor Therapy for Subfoveal Choroidal Neovascularization Secondary to Age-related Macular Degeneration," *Ophthalmology*, 2003, 110(5):979-86.
Hosoya et al., 2000, "Molecular and Functional Characteristics of APJ," *The Journal of Biological Chemistry*, 275(28):21061-21067.
Katugampola et al., 2001, "[$^{125}$I]-(Pyr$^1$)Apelin-13 is a novel radioligand for localizing the APJ orphan receptor in human and rat tissues with evidence for a vasoconstrictor role in man," *British Journal of Pharmacology*, 132:1255-1260.
Saint-Geniez et al., 2002, "Expression of the murine *msr/apj* receptor and its ligand apelin is upregulated during formation of the retinal vessels," *Mechanisms of Development*, 110:183-186.
Kalin et al., 2007, "Paracrine and Autocrine Mechanisms of Apelin Signaling Govern Embryonic and Tumor Angiogenesis," Developmental Biology, 305:599-614.

(Continued)

*Primary Examiner*—Lynn Bristol
(74) *Attorney, Agent, or Firm*—Sutherland Asbill & Brennan LLP

(57) ABSTRACT

Novel methods of inhibiting angiogenesis or tumorigenesis with compositions that inhibit the apelin/APJ signaling pathway are provided. Also provided are methods of promoting angiogenesis or tumorigenesis with compositions comprising an apelin polypeptide or small molecule agonist. The present invention further provides methods for identifying therapeutic agents that affect angiogenesis.

13 Claims, 12 Drawing Sheets

OTHER PUBLICATIONS

Kleinz et al., 2004, "Immunocytochemical Localization of the Endogenous Vasoactive Peptide Apelin to Human Vascular and Endocardial Endothelial Cells," Regulatory Peptides, 118:119-125.

Levine et al., 2003, "Fluorescent Labeling of Endothelial Cells Allow in vivo, Continuous Characterization of the Vascular Development of Xenopus Laevis," Developmental Biology, 254:50-67.

O'Dowd et al., 1993, "A Human Gene that Shows Identity with the Gene Encoding the Angiotensin Receptor is Located on Chromosome 11," Gene, 136:355-360.

Sorli et al., 2007, "Apelin is a Potent Activator of Tumour Neoangiogenesis," Oncogene (2007), 1-8.

Sorli et al., 2006, "Therapeutic Potential of Interfering with Apeling Signalling," Drug Discovery Today, 11 (23/24):1100-1106.

* cited by examiner

FIGURE 1

| | |
|---|---|
| RQRPRLSHKGPMPF | Frog |
| RQRPRLSHKGPMPF | Consensus |
| RQRPRLSHKGPMPF | Human |

RT-PCR analysis of APJ and apelin expression in adult mouse tissue and in a mouse endothelial cell line.

A. RT-PCR detection of APJ transcripts

PCR product from aorta has been sequenced and confirmed as APJ.

B. RT-PCR detection of Apelin transcripts

Asterisks mark correct size apelin PCR products

A

B

Apelin probe  A

VEGF probe  B

METHODS FOR MODULATING ANGIOGENESIS WITH APELIN COMPOSITIONS

This application claims priority to U.S. Provisional Application Ser. No. 60/528,155 filed Dec. 9, 2003 and U.S. Provisional Application Ser. No. 60/454,034 filed Mar. 12, 2003, both of which are hereby incorporated in their entirety.

ACKNOWLEDGEMENT OF FEDERAL RESEARCH SUPPORT

This invention was made, at least in part, with funding from National Institutes of Health (NIH Grant Number HL64763 and HL74184 to PK). Accordingly, the United States Government has certain rights in this invention.

BACKGROUND OF THE INVENTION

1. Field of the Invention

This invention relates generally to methods for modulating angiogenesis, tumorigenesis, and/or vascular permeability. In particular, this invention relates to methods for the use of compositions that affect the apelin/APJ signaling pathway to treat patients suffering from various angiogenesis-related diseases or conditions.

2. Background Art

Under normal physiological conditions, humans and animals undergo angiogenesis only in very specific situations. For example, angiogenesis is normally observed in wound healing, fetal and embryonic development, and formation of the corpus luteum, endometrium, and placenta. Unregulated angiogenesis occurs in a number of diseases and conditions, such as tumor growth and metastasis. Both controlled and unregulated angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

APJ is a cell surface receptor belonging to the G protein-coupled receptor family and has seven transmembrane domains. APJ is related to the angiotensin II receptor and has been described as being a coreceptor involved in the mediation of HIV-1 neuropathogenesis. A natural ligand of APJ was identified and named apelin (APJ endogenous ligand). The apelin polypeptide is initially produced as a 77 amino acid protein (preproapelin) that is cleaved to produce cleavage products of 36 amino acids, 17 amino acids, and 13 amino acids. The peptide consisting of the C-terminal 13 amino acids of the apelin polypeptide is necessary and sufficient for the ability of an apelin polypeptide to interact with APJ.

Some methods have been achieved which effectively modulate angiogenesis under certain conditions. For example, AVASTIN is an anti-VEGF antibody produced by Genentech that is currently in clinical trials for treatment of breast cancer, colorectal cancer, small cell lung cancer, and renal cancer, and that has been shown to have an anti-angiogenic effect on certain tumor types. AVASTIN has received FDA approval for use in patients having a colorectal cancer that has disseminated. Similarly, MACUGEN is an aptamer from Eyetech/Pfizer that targets VEGF and that has a demonstrated anti-angiogenic effect with regard to macular degeneration (Eyetech Study Group, 2003, Opthalmology 110(5):979-86).

To date, various polypeptides have been described that stimulate angiogenesis (e.g. VEGFs, FGFs, PDGFB, EGF, LPA, HGF, PD-ECF, IL-8, angiogenin, TNF-alpha, TGF-beta, TGF-alpha, proliferin, and PLGF) or inhibit angiogenesis (e.g. ENDOSTATIN, ANGIOSTATIN, and thrombospondin). Although some methods have been achieved which effectively modulate angiogenesis in certain situations, clearly more therapeutics are needed to treat a broader range of diseases and conditions, as well as to increase the efficacy of the methods that already exist. Therefore, what is needed in the art are new compositions and methods for modulating angiogenesis to inhibit the undesired growth of blood vessels associated with certain diseases and conditions. What is also needed are methods and compositions for modulating tumorigenesis and/or permeability of a tumor. What is further needed are new methods for promoting angiogenesis in patients suffering from diseases or conditions that are indicated by decreased vascularization. Moreover, what is also needed are methods for identifying therapeutic agents capable of modulating angiogenesis effectively and safely in a patient.

SUMMARY OF THE INVENTION

This invention fulfills in part the need to identify new, unique methods for modulating angiogenesis, tumorigenesis, and/or tumor permeability. In particular, the present invention describes methods for inhibiting angiogenesis or tumorigenesis in a biological sample, comprising providing a biological sample; and combining the sample with an angiogenesis-inhibiting or tumorigenesis-inhibiting amount of a composition comprising an inhibitor of apelin activity. In one embodiment, the composition comprising an inhibitor of apelin activity decreases the vascular permeability of a biological sample. In a preferred embodiment, the composition interferes with the interaction of an apelin polypeptide or apelin peptide with a receptor for apelin. In a more preferred embodiment, the composition interferes with the interaction of apelin with APJ. In another preferred embodiment, the composition comprises an anti-apelin antibody or fragment thereof. In a more preferred embodiment, the antibody binds a polypeptide or peptide selected from the group consisting of a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with any of the polypeptides or peptides above. In yet another preferred embodiment, the inhibitor of apelin activity is selected from the group consisting of apelin antisense nucleic acid, receptor decoy, ribozyme, sense polynucleotide, double stranded RNA, RNAi, aptamer, and small molecule antagonist.

The present invention provides that in some embodiments, the methods for inhibiting angiogenesis are used to treat a patient with disease or condition that involves angiogenesis. The present invention also provides that in some embodiments, the compositions comprise a combination of anti-angiogenic molecules, including a molecule that inhibits apelin activity and a molecule that inhibits another angiogenic factor. In other embodiments, the methods further comprise administering to the patient a therapeutically effective amount of an anti-cancer agent, wherein the anti-cancer agent is selected from the group consisting of a chemotherapeutic agent, a radiotherapeutic agent, an anti-angiogenic agent, and an apoptosis-inducing agent.

The present invention also provides methods for promoting angiogenesis in a biological sample, comprising providing a biological sample; and combining the sample with a biologically effective amount of an angiogenesis promoting composition comprising apelin. In a preferred embodiment, the composition comprises a polypeptide or peptide selected from the group consisting of a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with any of the polypeptides or peptides above. The present invention further provides methods of promoting angiogenesis in a patient that has a disease or condition that is indicated by decreased vascularization. The present invention also provides that in some embodiments, the compositions comprise a combination of angiogenic molecules, including apelin or an apelin agonist and another angiogenic factor.

The present invention also provides methods for identifying a modulator of angiogenesis, comprising providing an angiogenesis promoting composition comprising apelin; combining a putative modulator of angiogenesis with the composition; introducing the composition or the combination of the putative modulator and the composition to an angiogenesis predictive model; and comparing the amount of vascular branching in the model in the presence and absence of the putative modulator. In preferred embodiments, the apelin composition comprises a polypeptide or peptide selected from the group consisting of a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with any of the polypeptides or peptides above.

These and other embodiments of the invention will become apparent to one of skill in the art upon review of the description of the invention.

BRIEF DESCRIPTION OF THE DRAWINGS

FIG. 1 is an amino acid sequence alignment of the C-terminal thirteen amino acids of the frog apelin polypeptide (SEQ ID NO:18), the human apelin polypeptide (residues 23-36 of SEQ ID NO:2), and the consensus sequence (SEQ ID NO:19), showing that the C-terminal thirteen amino acids are identical between the two sequences.

FIG. 10A is an autoradiograph (17 hour exposure) of a dot blot membrane hybridized with an approximately 2 kb $^{32}$P-labeled apelin probe. FIG. 10B is an autoradiograph (17 hour exposure) of a dot blot membrane hybridized with an approximately 700 base $^{32}$P-labeled VEGF-A probe.

Figure 2:
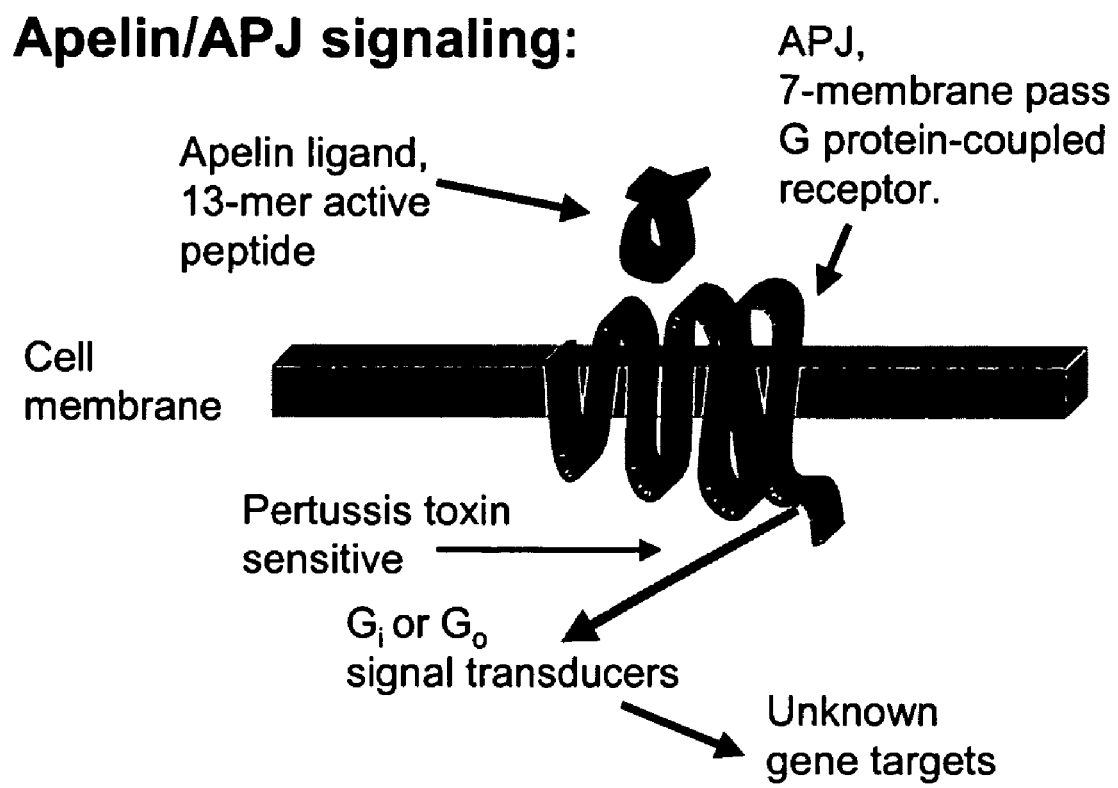
FIG. 2 is a schematic representation of the apelin/APJ signaling pathway.

for four days. Medium was removed, and cells were treated with fresh media (U) or fresh media containing 150 μM Cobalt Chloride (Co) (Piret et al., 2002). Panel A shows the electrophoretic gel of PCR products generated using the GADPH primer set; panel B shows the electrophoretic gel of PCR products generated using the GADPH primer set; and panel C shows the electrophoretic gel of PCR products generated using the GADPH primer set.

DETAILED DESCRIPTION OF THE INVENTION

The present invention may be understood more readily by reference to the following detailed description of the preferred embodiments of the invention and the Examples included herein. However, before the present methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is further to be understood that unless specifically defined herein, the terminology used herein is to be given its traditional meaning as known in the relative art.

The present invention describes for the first time that the apelin peptide is useful in modulating angiogenesis. In certain preferred embodiments, the present invention describes methods for inhibiting angiogenesis, inhibiting tumorigenesis, or decreasing vascular permeability in a biological sample, comprising providing a biological sample; and combining the sample with an angiogenesis-inhibiting, tumorigenesis-inhibiting, and/or vascular permeability-decreasing amount of a composition comprising an inhibitor of apelin activity. As used herein, the term "angiogenesis" refers to the generation of new blood vessels, and the term "tumorigenesis" refers to the growth of a tumor. As also used herein, the phrase "methods for inhibiting angiogenesis or tumorigenesis" is intended to include methods that inhibit angiogenesis or tumorigenesis by decreasing vascular permeability. As also used herein, the term "apelin polypeptide" is intended to refer to a polypeptide that comprises the C-terminal 13 amino acids of apelin (i.e. the polypeptide of SEQ ID NO:4). In a preferred embodiment, the composition interferes with the interaction of an apelin polypeptide or apelin peptide with a receptor for apelin. In another preferred embodiment, the composition interferes with the interaction of an apelin polypeptide or apelin peptide with APJ. In another preferred embodiment, the composition comprises an anti-apelin antibody or fragment thereof. In a preferred embodiment, the antibody binds a polypeptide or peptide selected from the group consisting of a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with any of the polypeptides or peptides above. As used herein, the phrase "antibody fragment" is intended to include various fragments of an antibody including, but not limited to, $F_{ab}$ fragments, $F_{ab'}$ fragments, $F_{(ab')2}$ fragments, and smaller fragments such as those described by Domantis. In another preferred embodiment, the composition comprises an apelin antisense nucleic acid.

In another preferred embodiment, the inhibitor of apelin activity is selected from the group consisting of apelin antisense nucleic acid, receptor decoy, ribozyme, sense polynucleotide, double stranded RNA, RNAi, aptamer, and small molecule antagonist. As used herein, the term "receptor decoy" refers to a molecule that will bind to an apelin polypeptide and prevent the apelin polypeptide from participating in its native signaling pathway(s). A receptor decoy is intended to encompass a soluble receptor for apelin (or fragment thereof) which is capable of binding apelin in the serum and inhibiting apelin from signaling through its native signaling pathway(s).

The present invention also provides that in some embodiments, the compositions comprise a combination of anti-angiogenic molecules, including a molecule that inhibits apelin activity and a molecule that inhibits another angiogenic factor. As used herein, the term "angiogenic factor" is intended to include molecules that promote angiogenesis, such as, for example, VEGFs, FGFs, PDGFB, EGF, LPA, HGF, PD-ECF, IL-8, angiogenin, TNF-alpha, TGF-beta, TGF-alpha, proliferin, and PLGF.

In other preferred embodiments of the present invention, the compositions used inhibit apelin activity by interfering with a receptor for apelin. In one embodiment, the receptor for apelin is APJ. In certain preferred embodiments, the inhibitor of apelin activity is an anti-APJ antibody or fragment thereof. In a more preferred embodiment, inhibitor of apelin activity is an antibody or fragment thereof that binds a polypeptide as defined in SEQ ID NO: 17. In other preferred embodiments, the inhibitor of apelin activity is selected from the group consisting of an APJ antisense nucleic acid, receptor decoy, ribozyme, sense polynucleotide, double stranded RNA, RNAi, aptamer, and small molecule antagonist.

In certain preferred embodiments of the present invention, the compositions comprise a combination of anti-angiogenic molecules, including a molecule that inhibits APJ activity and a molecule that inhibits another angiogenic factor. In a more preferred embodiment, the angiogenic factor is selected from the group consisting of VEGFs, FGFs, PDGFB, EGF, LPA, HGF, PD-ECF, IL-8, angiogenin, TNF-alpha, TGF-beta, TGF-alpha, proliferin, and PLGF.

In certain preferred embodiments of the present invention, the methods for inhibiting angiogenesis or tumorigenesis are used to treat a patient with disease or condition that involves angiogenesis or tumorigenesis. As used herein, the phrase "disease or condition involving angiogenesis" is intended to include, but is not limited to, stroke, hemangioma, solid tumors, leukemias, lymphomas, myelomas, metastasis, telangiectasia psoriasis scleroderma, pyogenic granuloma, Myocardial angiogenesis, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, placentation, polycystic ovary syndrome, dysfunctional uterine bleeding, endometrial hyperplasia and carcinoma, endometriosis, failed implantation and subnormal foetal growth, myometrial fibroids (uterine leiomyomas) and adenomyosis, ovarian hyperstimulation syndrome, and ovarian carcinoma. In other preferred embodiments of the present invention, the methods for inhibiting angiogenesis or tumorigenesis are used to treat a patient with disease or condition that involves tumorigenesis. In other preferred embodiments of the present invention, the methods for inhibiting angiogenesis or tumorigenesis are used to treat a patient with disease or condition that involves inappropriate leakage of blood vessels. In a more preferred embodiment, the apelin-inhibiting composition used in the methods for inhibiting angiogenesis or tumorigenesis acts by decreasing vascular permeability.

In certain preferred embodiments of the present invention, the methods further comprise administering to the patient a therapeutically effective amount of an anti-cancer agent, wherein the anti-cancer agent is selected from the group consisting of a chemotherapeutic agent, a radiotherapeutic agent, an anti-angiogenic agent, an apoptosis-inducing agent. As used herein, a "therapeutically effective amount" is an amount which has a negative effect on angiogenesis or tumor growth. As also used herein, an "anti-cancer agent" refers to a molecule which has a negative effect on angiogenesis or tumor growth. In one embodiment, the anti-cancer agent is an anti-angiogenic agent that inhibits the expression or activity of an angiogenic factor selected from the group consisting of VEGFs, FGFs, PDGFB, EGF, LPA, HGF, PD-ECF, IL-8, angiogenin, TNF-alpha, TGF-beta, TGF-alpha, proliferin, and PLGF. In another embodiment, the anti-cancer agent is an anti-angiogenic agent selected from the group consisting of an agent that inhibits the expression or activity of a matrix metalloproteinase; an agent that interacts with a cell adhesion molecule; and an agent that inhibits the activity of a urokinase; and an agent that inhibits angiogenesis through another mechanism.

The present invention also provides methods for promoting angiogenesis in a biological sample, comprising providing a biological sample; and combining the sample with a biologically effective amount of an angiogenesis promoting composition comprising apelin. In a preferred embodiment, the composition comprises a polypeptide or peptide selected from the group consisting of a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with any of the polypeptides or peptides above. The present invention also provides that in some embodiments, the compositions comprise a combination of angiogenic molecules, including apelin (or an apelin agonist) and another angiogenic factor.

In certain preferred embodiments of the present invention, the methods for promoting angiogenesis are used to treat a patient with disease or condition that is indicated by decreased vascularization. As used herein, the phrase "disease or condition involving angiogenesis" is intended to include, but is not limited to, diabetes, arthritis, ischemia, anemia, a wound, gangrene, or necrosis.

As used herein, the terms "peptide," "polypeptide," and "protein" refer to a chain of at least four amino acids joined by peptide bonds. The chain may be linear, branched, circular, or combinations thereof. Accordingly, the present invention provides methods for the use of isolated apelin polypeptides and APJ polypeptides. In preferred embodiments, the apelin polypeptide is defined in SEQ ID NO: 1, SEQ ID NO:2, SEQ ID NO:3, SEQ ID NO:4, or SEQ ID NO:5; and the APJ polypeptide is defined in SEQ ID NO:17.

The apelin polypeptide of the present invention, and fragments thereof, are preferably synthesized chemically by standard peptide synthesis techniques. For the purposes of this invention, when chemically synthesized, the apelin-13 peptide may comprise a pyroglutamate rather than a glutamic acid residue in the N-terminal position. As an alternative to standard peptide synthesis, an apelin polypeptide, or peptide thereof, can be produced using standard recombinant DNA techniques. For example, a nucleic acid molecule encoding the polypeptide is cloned into an expression vector, the expression vector is introduced into a host cell, and the apelin polypeptide is expressed in the host cell. The apelin polypeptide can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. The apelin polypeptide of the present invention, and fragments thereof, are preferably produced using standard recombinant techniques. Moreover, native apelin or APJ polypeptide can be isolated from cells, for example, using an anti-apelin or anti-APJ antibody, respectively.

As used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

A nucleic acid molecule of the present invention, or a portion thereof, can be isolated using standard molecular biology techniques and the sequence information provided herein. For example, an apelin cDNA can be isolated from a cDNA library using all or portion of a polynucleotide sequence encoding one of the polypeptides of SEQ ID NO: 1, SEQ ID NO:2, SEQ ID NO:3, SEQ ID NO:4, or SEQ ID NO:5. Moreover, a nucleic acid molecule encompassing all or a portion of an apelin polypeptide can be isolated by the polymerase chain reaction (PCR) using oligonucleotide primers designed based upon the sequences provided herein. For example, mRNA can be isolated from a cell, and synthetic oligonucleotide primers for PCR amplification can be designed based upon a polynucleotide sequence encoding one of the polypeptide sequences shown in SEQ ID NO: 1, SEQ ID NO:2, SEQ ID NO:3, SEQ ID NO:4, SEQ ID NO:5, or SEQ ID NO:17. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an apelin nucleotide sequence can be prepared by standard synthetic techniques, e.g., using an automated DNA synthesizer.

As used herein, the term "biologically active portion of" an apelin is intended to include a portion, e.g., a domain/motif of an apelin that participates in the interaction with APJ and/or the modulation of APJ activity. Biologically active portions of an apelin include peptides comprising amino acid sequences derived from the amino acid sequence of an apelin, e.g., an amino acid sequence of SEQ ID NO: 1, SEQ ID NO:2, SEQ ID NO:3, SEQ ID NO:4, or SEQ ID NO:5, or the amino acid sequence of a polypeptide identical to an apelin, which includes fewer amino acids than a full length apelin or the full length polypeptide which is identical to an apelin polypeptide, and exhibits at least one activity of an apelin polypeptide. As also used herein, the term "biologically active portion of" APJ is intended to include a portion, e.g., a domain/motif of APJ that participates in the interaction of APJ with apelin and/or the modulation of the apelin/APJ signaling pathway. Biologically active portions of APJ include peptides comprising amino acid sequences derived from the amino acid sequence of APJ, e.g., an amino acid sequence of SEQ ID NO: 17, or the amino acid sequence of a polypeptide identical to APJ, which includes fewer amino acids than a full length APJ or the full length polypeptide which is identical to an APJ polypeptide, and exhibits at least one activity of an APJ polypeptide. Typically, biologically active portions (e.g., peptides which are, for example, 5, 10, 15, 20, 30, 35, 36, 37, 38, 39, 40, or more amino acids in length) comprise a domain or motif with at least one activity of an apelin polypeptide. As used herein, the terms "apelin activity" and "APJ activity" are intended to refer to the promotion of angiogenesis or tumorigenesis. As also used herein, the term "apelin/APJ signaling pathway" refers to the signal transduction pathway involving the interaction of apelin and APJ by which angiogenesis is promoted. For the purposes of the present invention, modulation of apelin or APJ activity refers to at least a 10% increase or decrease in angiogenesis in the presence of a composition as compared to angiogenesis in the absence of the composition.

The invention also provides the use of apelin or APJ chimeric or fusion polypeptides. For example, as used herein, an apelin "chimeric polypeptide" or "fusion polypeptide" comprises an apelin polypeptide or peptide operatively linked to a non-apelin polypeptide. An apelin polypeptide refers to a polypeptide having an amino acid sequence corresponding to an apelin polypeptide, whereas a non-apelin polypeptide refers to a polypeptide having an amino acid sequence corresponding to a polypeptide which is not substantially identical to the apelin polypeptide, e.g., a polypeptide that is different from the apelin and is derived from the same or a different organism. With respect to the fusion polypeptide, the term "operatively linked" is intended to indicate that the apelin polypeptide and the non-apelin polypeptide are fused to each other so that both sequences fulfill the proposed function attributed to the sequence used. The non-apelin polypeptide can be fused to the N-terminus or C-terminus of the apelin polypeptide. For example, in one embodiment, the fusion polypeptide is a GST-apelin fusion polypeptide in which the apelin sequences are fused to the C-terminus of the GST sequences. Such fusion polypeptides can facilitate the purification of recombinant apelin polypeptides. In another embodiment, the fusion polypeptide is an apelin polypeptide containing a heterologous signal sequence at its N-terminus. In certain host cells (e.g., mammalian host cells), expression and/or secretion of an apelin polypeptide can be increased through use of a heterologous signal sequence.

Preferably, an apelin or APJ chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992). Moreover, many expression vectors are commercially available that already encode a fusion moiety (e.g., a GST polypeptide). An apelin encoding nucleic acid can be cloned into such an expression vector such that the fusion moiety is linked in-frame to the apelin polypeptide.

In addition to fragments and fusion polypeptides of the apelin polypeptides described herein, the present invention includes homologs and analogs of naturally occurring apelin or APJ polypeptides and apelin or APJ encoding nucleic acids in the same or other organisms. "Homologs" are defined herein as two nucleic acids or polypeptides that have similar or "identical," nucleotide or amino acid sequences, respectively. Homologs include allelic variants, orthologs, paralogs, agonists, and antagonists of apelin or APJ as defined hereafter. The term "homolog" further encompasses nucleic acid molecules that differ from a first nucleic acid (and portions thereof) due to degeneracy of the genetic code and thus encode the same polypeptide. As used herein, a "naturally occurring" apelin or APJ polypeptide refers to an apelin or APJ amino acid sequence that occurs in nature. Preferably, a naturally occurring apelin comprises an amino acid sequence as defined in SEQ ID NO: 1, SEQ ID NO:2, SEQ ID NO:3, SEQ ID NO:4, or SEQ ID NO:5; and a naturally occurring APJ comprises the amino acid sequence as defined in SEQ ID NO: 17.

An agonist of the apelin or APJ polypeptide can retain substantially the same, or a subset, of the biological activities of the apelin or APJ polypeptide. An antagonist of the apelin or APJ polypeptide can inhibit one or more of the activities of the naturally occurring form of the apelin or APJ polypeptide. For example, the apelin antagonist can competitively bind to a downstream or upstream member of the cell membrane component metabolic cascade that includes the apelin polypeptide.

In another embodiment of the present invention, the compositions used may inhibit or promote apelin activity indirectly. For example, the compositions may comprise a specific endopeptidase or endopeptidase inhibitor. In particular, the endopeptidase to be used belongs to the subtilisin family of serine proteases (Barr, 1991, Cell 66:1-3). These enzymes cleave specifically after arginine residues (e.g. KR, RR, KXKR, RXRR, KKKR (SEQ ID NO:20), RRRR (SEQ ID NO:21), KXXR, and RXXR) and are likely involved in the cleavage of apelin to the 13 amino acid and 17 amino acid peptides.

As stated above, the present invention includes apelin and APJ polypeptides and homologs thereof. To determine the percent sequence identity of two amino acid sequences (e.g., one of the sequences of SEQ ID NO:1, SEQ ID NO:2, SEQ ID NO:3, SEQ ID NO:4, SEQ ID NO:5, or SEQ ID NO:17, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:1, SEQ ID NO:2, SEQ ID NO:3, SEQ ID NO:4, SEQ ID NO:5, or SEQ ID NO:17) is occupied by the same amino acid residue as the corresponding position in the other sequence (e.g., a mutant form of the sequence of SEQ ID NO:1, SEQ ID NO:2, SEQ ID NO:3, SEQ ID NO:4, SEQ ID NO:5, or SEQ ID NO: 17), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO: 1, SEQ ID NO:2, SEQ ID NO:3, SEQ ID NO:4, SEQ ID NO:5, or SEQ ID NO:17. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO: 1, SEQ ID NO:2, SEQ ID NO:3, SEQ ID NO:4, SEQ ID NO:5, or SEQ ID NO:17. In other embodiments, the apelin amino acid homologs have sequence identity over at least 5 contiguous amino acid residues, more preferably at least 10 contiguous amino acid residues, and most preferably at least 13 contiguous amino acid residues of SEQ ID NO: 1, SEQ ID NO:2, SEQ ID NO:3, SEQ ID NO:4, SEQ ID NO:5, or SEQ ID NO:17.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence of the present invention, or to a portion comprising at least 39 consecutive nucleotides thereof.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to a polynucleotide of the present invention under stringent conditions. As used herein with regard to hybridization for DNA to a DNA blot, the term "stringent conditions" refers to hybridization overnight at 60° C. in 10× Denhart's solution, 6×SSC, 0.5% SDS, and 100 μg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, "highly stringent conditions" refers to hybridization overnight at 65° C. in 10× Denharts solution, 6×SSC, 0.5% SDS, and 100 μg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, N.Y., 1993.

Using the above-described methods, and others known to those of skill in the art, one of ordinary skill in the art can isolate homologs of the apelin or APJ polypeptides comprising amino acid sequences shown in SEQ ID NO:1, SEQ ID NO:2, SEQ ID NO:3, SEQ ID NO:4, SEQ ID NO:5, or SEQ ID NO:17. One subset of these homologs is allelic variants. As used herein, the term "allelic variant" of apelin refers to a nucleotide sequence containing polymorphisms that lead to changes in the amino acid sequences of an apelin polypeptide and that exist within a natural population. Such natural allelic variations can typically result in 1-6% variance in an apelin nucleic acid. Any and all such nucleic acid variations and resulting amino acid polymorphisms or variations in an apelin that are the result of natural allelic variation and that do not alter the functional activity of an apelin, are intended to be within the scope of the methods of the present invention.

Analogs, orthologs, and paralogs of a naturally occurring apelin or APJ polypeptide can differ from the naturally occurring apelin by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring apelin or APJ amino acid sequence, and will exhibit a function similar to an apelin or APJ polypeptide. Preferably, an apelin ortholog of the present invention functions by interacting with APJ and by affecting angiogenesis or tumorigenesis.

In addition to naturally-occurring variants of an apelin or APJ sequence that may exist in the population, the skilled artisan will further appreciate that changes can be introduced by mutation into a nucleotide sequence encoding the polypeptides of SEQ ID NO:1, SEQ ID NO:2, SEQ ID NO:3, SEQ ID NO:4, SEQ ID NO:5, or SEQ ID NO:17, thereby leading to changes in the amino acid sequence of the encoded apelin or APJ polypeptide, without altering the functional activity of the apelin or APJ. For example, nucleotide substitutions leading to amino acid substitutions at "non-essential" amino acid residues can be made in a sequence of SEQ ID NO:1, SEQ ID NO:2, SEQ ID NO:3, SEQ ID NO:4, SEQ ID NO:5, or SEQ ID NO:17. A "non-essential" amino acid residue is a residue that can be altered from the wild-type sequence of one of the apelin or APJ polypeptides without altering the activity of said apelin or APJ polypeptide, whereas an "essential" amino acid residue is required for apelin or APJ activity. Other amino acid residues, however, (e.g., those that are not conserved or only semi-conserved in the domain having apelin or APJ activity) may not be essential for activity and thus are likely to be amenable to alteration without altering apelin or APJ activity.

The present invention also includes polypeptides having a conservative amino acid substitution in one of the sequences of SEQ ID NO:1, SEQ ID NO:2, SEQ ID NO:3, SEQ ID NO:4, SEQ ID NO:5, or SEQ ID NO:17. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an apelin polypeptide is preferably replaced with another amino acid residue from the same side chain family. Alternatively, in another embodiment, mutations can be introduced randomly along all or part of an apelin coding sequence, such as by saturation mutagenesis, and the resultant mutants can be screened for an apelin activity described herein to identify mutants that retain apelin activity.

Another aspect of the invention pertains to the use of isolated nucleic acid molecules that are antisense to an apelin coding sequence. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame. In another preferred embodiment, the present invention provides that the target regions may be within the 3' UTR region, or the target regions may be in any region of the mRNA transcript.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. In addition to these standard rules, with respect to RNA, guanine also may be paired with uracil (G:U) in some cases. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO: 1, SEQ ID NO:2, SEQ ID NO:3, SEQ ID NO:4, SEQ ID NO:5, or SEQ ID NO:17.

The antisense nucleic acid can be complementary to an entire apelin coding strand, or to only a portion thereof. In one embodiment, an antisense nucleic acid molecule is antisense to a "coding region" of the coding strand of a nucleotide sequence encoding an apelin. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding an apelin. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of apelin mRNA, but more preferably is an oligonucleotide that is antisense to only a portion of the coding or noncoding region of apelin mRNA. For example, the antisense oligonucleotide can be complementary to the region surrounding the translation start site of apelin mRNA. An antisense oligonucleotide can be, for example, about 5, 10, 15, 20, 25, 30, 35, or more nucleotides in length. Typically, the antisense molecules of the present invention comprise an RNA having 60-100% sequence identity with at least 10 consecutive nucleotides of a polynucleotide encoding a polypeptide of SEQ ID NO:1, SEQ ID NO:2, SEQ ID NO:3, SEQ ID NO:4, SEQ ID NO:5, or SEQ ID NO: 17. Preferably, the sequence identity will be at least 70%, more preferably at least 75%, 80%, 85%, 90%, 95%, 96%, 97%, 98%, or 99%, and most preferably 100%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641).

The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding an apelin or APJ to thereby inhibit expression of the polypeptide, e.g., by inhibiting transcription, by inhibiting translation, and/or by causing transcript degradation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of an apelin or APJ polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave apelin or APJ mRNA transcripts to thereby inhibit translation of apelin or APJ mRNA. A ribozyme having specificity for an apelin-encoding or APJ-encoding nucleic acid can be designed based upon the nucleotide sequence of an apelin or APJ cDNA or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an apelin-encoding mRNA. See, e.g., U.S. Pat. Nos. 4,987,071 and 5,116,742 to Cech et al. Alternatively, apelin mRNA can be used to select a catalytic RNA having a specific ribonuclease activity from a pool of RNA molecules. See, e.g., Bartel, D. and Szostak, J. W., 1993, Science 261: 1411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

Alternatively, apelin or APJ gene expression can be inhibited by targeting nucleotide sequences complementary to the regulatory region of an apelin or APJ nucleotide sequence (e.g., an apelin or APJ promoter and/or enhancer) to form triple helical structures that prevent transcription of an apelin gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In addition to the use of apelin and APJ nucleic acids and polypeptides described above, the present invention encompasses the use of these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide that hybridizes under stringent conditions to the desired nucleic acid. In preferred embodiments, the probe further comprises a label group attached thereto, e.g. the label group can be a radioisotope, a fluorescent compound, an enzyme, or an enzyme co-factor.

In certain preferred embodiments of the present invention, the methods further comprise administering to the patient a therapeutically effective amount of an anti-cancer agent, wherein the anti-cancer agent is selected from the group consisting of a chemotherapeutic agent, a radiotherapeutic agent, an anti-angiogenic agent, an apoptosis-inducing agent. In one embodiment, the anti-cancer agent is an anti-angiogenic agent that inhibits the expression or activity of an angiogenic factor selected from the group consisting of VEGFs, FGFs, PDGFB, EGF, LPA, HGF, PD-ECF, IL-8, angiogenin, TNF-alpha, TGF-beta, TGF-alpha, proliferin, and PLGF.

Another aspect of the invention pertains to the use of isolated apelin polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of apelin in which the polypeptide is separated from some of the cellular components of the cells in which it is naturally or recombinantly produced. In one embodiment, the language "substantially free of cellular material" includes preparations of an apelin having less than about 30% (by dry weight) of non-apelin material (also referred to herein as a "contaminating polypeptide"), more preferably less than about 20% of non-apelin material, still more preferably less than about 10% of non-apelin material, and most preferably less than about 5% non-apelin material.

When the apelin or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of apelin polypeptide in which the polypeptide is separated from chemical precursors or other chemicals that are involved in the synthesis of the polypeptide. In one embodiment, the language "substantially free of chemical precursors or other chemicals" includes preparations of an apelin polypeptide having less than about 30% (by dry weight) of chemical precursors or other chemicals, more preferably less than about 20% chemical precursors or other chemicals, still more preferably less than about 10% chemical precursors or other chemicals, and most preferably less than about 5% chemical precursors or other chemicals. In preferred embodiments, isolated polypeptides, or biologically active portions thereof, lack contaminating polypeptides from the same organism from which the apelin is derived.

The present invention also provides the use of antibodies that specifically bind to an apelin polypeptide, or a portion thereof. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10:163-167; Bebbington et al., 1992, Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

The compositions of this invention further comprises a pharmaceutically acceptable carrier. The phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein with respect to these methods, the term "administering" refers to various means of introducing a composition into a cell or into a patient. These means are well known in the art and may include, for example, injection; tablets, pills, capsules, or other solids for oral administration; nasal solutions or sprays; aerosols, inhalants; topical formulations; liposomal forms; and the like. As used herein, the term "effective amount" refers to an amount that will result in the desired result and may readily be determined by one of ordinary skill in the art.

The compositions of the present invention (e.g. angiogenesis-inhibiting, angiogenesis-promoting, and tumorigenesis-inhibiting) may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains such an apelin peptide, anti-apelin antibody or antibody fragment, anti-APJ antibody or antibody fragment, apelin or APJ antisense nucleic acid, apelin receptor decoy, ribozyme, sense polynucleotide, double stranded RNA, RNAi, aptamer, or small molecule agonist, as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention (e.g. angiogenesis-inhibiting, angiogenesis-promoting, and tumorigenesis-inhibiting) can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention (e.g. angiogenesis-inhibiting, angiogenesis-promoting, and tumorigenesis-inhibiting) should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active ingredient (e.g. the apelin peptide, anti-apelin antibody or antibody fragment, anti-APJ antibody or antibody fragment, apelin or APJ antisense nucleic acid, apelin receptor decoy, ribozyme, sense polynucleotide, double stranded RNA, RNAi, aptamer, or small molecule agonist) admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

In one embodiment, the present invention provides methods of screening for a modulator of angiogenesis, comprising providing an angiogenesis promoting composition comprising apelin; combining a putative modulator of angiogenesis with the composition; introducing the composition or the combination of the putative modulator and the composition to an angiogenesis predictive model; and comparing the amount of vascular branching in the model in the presence and absence of the putative modulator. In a preferred embodiment, the composition comprises a polypeptide or peptide selected from the group consisting of: a polypeptide as defined in SEQ ID NO: 1; a polypeptide as defined in SEQ ID NO:2; a polypeptide as defined in SEQ ID NO:3; a polypeptide as defined in SEQ ID NO:4; a polypeptide as defined in SEQ ID NO:5; and a polypeptide having at least 80% sequence identity with a polypeptide or peptide of a) through c) above. In another preferred embodiment of the present invention, the angiogenesis predictive model is a chicken chorioallantoic membrane (CAM) assay.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

PCR Characterization of Apelin Expression and APJ Expression Distribution

Total RNA was isolated from mouse yolk sac tissue (positive control), mouse thoracic aorta (aorta), and a mouse brain endothelial cell line (bend.3) using a guanidinium isothiocyanate method (Chomczynski and Sacchi, 1987, Anal. Biochem. 162:156-159). cDNA was prepared from these tissues using standard methods, and RT-PCR amplification of APJ sequences using APJ specific primers was performed for 35 cycles.

Figure 3:
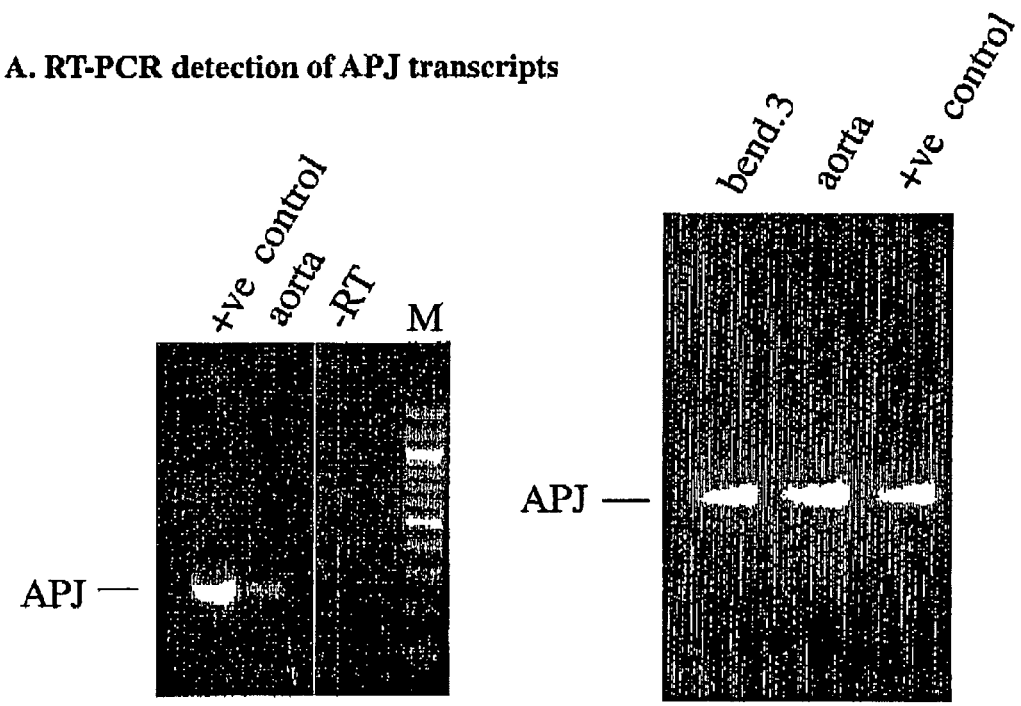
FIG. 3A are two photographs of electrophoretic gels, showing the RT-PCR detection of APJ transcripts in adult mouse tissue and a mouse endothelial cell line.
FIG. 3B is a photograph of an electrophoretic gel, showing the RT-PCR detection of apelin transcripts in an embryonic yolk sac and a mouse endothelial cell line.
Figure 3:
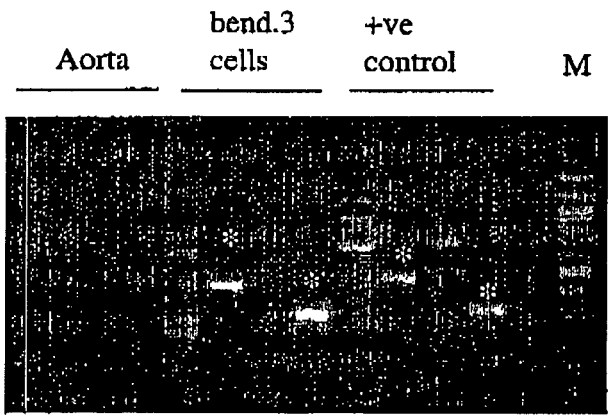

As shown on the left hand panel of FIG. 3A, APJ transcripts are present in aorta tissue of the adult mouse. The PCR product was isolated and the presence of APJ sequences were confirmed by DNA sequencing using standard methods. The right hand panel of FIG. 3A shows the results of an RT-PCR detection of APJ sequences and shows the presence of APJ transcripts in bend.3 cells (together with aorta and positive control samples).

The same cDNA samples used for detection of APJ sequences (above) were used as template for detection of apelin sequences. Four different primer pairs were used in this experiment, and all amplifications were carried out for 35 cycles. Note that the mouse aorta sample contained no detectable apelin sequences. In contrast, the bend.3 mouse endothelial cell line is positive for apelin sequences (indicated by asterisks). This result indicates that the bend.3 cell line expresses both apelin and the apelin receptor, APJ.

Example 2

In Situ Hybridization Analysis of Apelin Expression and APJ Expression Distribution In situ hybridization was performed on frog embryos, using an antisense probe directed against APJ transcripts.

Whole Mount In Situ Hybridization

In situ hybridization was performed by a modified version of the procedure described in Harland, R. M., 1991, Methods in Cell Biology 36:685-695 (modified version designed by Rob Garriock). In all steps of this protocol, embryos were stored in 4 ml glass screw capped tubes.

Embryos were fixed in a 4% PFA solution (25 ml of 8% PFA stock solution (filtered) in 1×PBS). Embryos or embryo bits were placed in an abundant volume of fixative and rocked gently for 2 hours at room temperature or overnight at 4° C. The fixative was replaced with methanol which had been cooled to −20° C. The embryos can then be stored for several months at −20° C.

Frozen embryos were rehydrated for staining through a series of washes. First, the embryos are washed for 2 minutes in 2 ml of a 75% Methanol:25% $H_2O$ solution followed by a 2 minute wash in 2 ml of a 50% Methanol:50% $H_2O$ solution. The embryos were then washed two times for 2 minutes each with TTW (200 mM NaCl, 50 mM Tris, pH. 7.4, 0.1% Tween-20). During the washes, the tubes were kept upright and rocked gently.

The embryos were placed in a vial with 5 µg/ml Proteinase K (1 µl of 25 mg/ml stock solution in 5 ml of TTW) for 5-30 minutes on a shaker or nutator. For embryos at Stages 10-20, this incubation was for 5 minutes. For embryos at Stages 20-34, this incubation was for 10 minutes; and for embryos at Stages 35-41, this incubation was for 15-30 minutes. Following the Proteinase K treatment, the embryos were washed once in TTW for 5 minutes. The embryos were then re-fixed in 1-2 ml PFA-fix (4% PFA in PBS) for 20 minutes at room temperature (or longer at 4° C.). Then the embryos were washed three times in TTW for 5 minutes each time to remove the PFA-fix.

The embryos were prehybridized by incubating them in 2 ml of RNA Hybridization buffer (50% formamide, 5×SSC, 1 mg/ml Yeast RNA, 1× Denhart's, 0.1% Tween-20, 5 mM EDTA) at 65° C. for 1 hour. After prehybridization, 500 µl-1 ml of probe was added, and the embryos were incubated for 4 hours to overnight. Excess probe was removed through a series of washes. First, the embryos were washed twice for 20 minutes each time in approximately 2 ml 2×SSC at 37° C. Then, the embryos were washed once for 30 minutes in 2 ml 2×SSC with 1 µl/5 ml of RNAse cocktail (Ambion Cat#2286=1 mg/ml RNAse A, 20,000 U/ml RNAse T1). Finally, the embryos were washed 2-3 times for 1 hour each time in a preheated 0.2×SSC+0.01% Tween-20 solution at 65° C.

The embryos were then incubated once for 20 minutes in 1-2 ml Maleic acid buffer (MAB buffer-5.8 g Maleic acid and 4.4 g NaCl in water for a total volume of 500 ml, pH 7.5) with 1-2% B&M Blocking reagent. At the same time, 0.5-1 µl of anti-Dig antibody was preblocked by adding the antibody to 5 ml of MAB-block and incubating for 20 minutes. Then the embryos were incubated 3 hours (at room temperature) or overnight (at 4° C.) in alkaline phosphatase-conjugated anti-digoxygenin antibody (1/5,000-10,000 dilution in MAB block (1 ml)). The antibody solution was removed, and the tubes were filled completely with MAB and rocked on a nutator on their sides. Alternatively, all washing steps could be performed without rocking. Two short washes were performed at room temperature before an overnight wash at 4° C., followed by 6 more washes (30 minutes each). In some instances, the embryos were washed 10 times (30 minutes each) at room temperature. An additional overnight wash in MAB will produce cleaner in situ results.

The embryos were then incubated for 10 minutes in fresh alkaline phosphatase buffer (APB)(100 mM Tris, pH 9.5, 50 mM MgCl2, 100 mM NaCl, 0.1% Tween-20) at room temperature. Alternatively, Levamisol was added to buffer just before use to a final concentration of 2 mM. The APB was exchanged with 1-2 ml alkaline phosphatase reaction buffer containing APB and nitro blue tetrazolium (NBT)/5-bromo-4-chloro-3-indolyl-phosphate (BCIP). For this reaction buffer, 2-4 µl NBT (75 mg/ml stock in 70% dimethyl formamide) and 2-4 µl BCIP (75 mg/ml stock in 100% dimethyl formamide) were added per 1 ml APB.

When the staining appears optimal, the following procedure was used for stopping the reaction, which tended to reduce background, especially ectodermal background, without any adverse effects on the staining intensity. By comparison to the procedure described below, the direct addition of Bouin's fixative (1 g Picric acid in 70 ml water or 70 ml of a 1.3% saturated solution, 25 ml of 37% formaldehyde, 5 ml of glacial acietic acid) caused a precipitate to form around the embryos which is hard to remove. The stained embryos were incubated for 1 hour in 100% Methanol to remove nonspecific staining. Then the embryos were washed for 2 minutes in 75% Methanol, followed by 2 minutes in 50% Methanol, and finally two washes for 5 minutes each in TTW. The embryos were fixed overnight in MEMPFA, and optionally with Bouin's fixative for yellow counterstain. MEMPFA fixed embryos were then washed in TTW, and viewed and stored in 50% glycerol. Alternatively, glycerol stored embryos could be parafin sectioned by washing a few times in TTW and dehydrating in ethanol. Bouin's fixative stops the reaction completely and gave a nice yellow background stain which contrasts well with the blue color reaction, but these embryos did not section well.

Before viewing and storing, the embryos were washed for 5 minutes in 25% Methanol, followed by 5 minutes in 50% Methanol, 5 minutes in 75% Methanol, before placing into 100% Methanol. If pigmented embryos were used, the pigmentation was reduced by exposing embryos to sunlight or other strong light source in a peroxide/formamide solution in methanol (1 ml of 30% $H_2O_2$, 10% Formamide, 70% Methanol). These embryos were bleached in the black screw tops placed on a tinfoil wrapped petri dish in order that the sunlight reflected back through the embryo and caused bleaching of both sides. Indoor lighting sources could also be used, however, it would take longer to bleach the embryo.

To clear embryos, embryos were transferred to a glass vial, and the solution was replaced with methanol with one part benzyl alcohol:two parts benzyl benzoate (BABB). The staining appears to fade in BABB especially when the embryos are left on a lit microscope so transfer back to methanol after viewing. This is ideal for deep staining but not very good for surface staining. Embryos were partially cleared in a 50-70% glycerol solution and easily positioned. Embryos must first be in buffer before transferring them into glycerol and must sit in glycerol for sometime until they equilibrated into the solution. Embryos could also be stored permanently in glycerol at 4° C. or −20° C. Uncleared embryos were photographed in a Methanol/Ethanol solution or straight TTW or PBS buffer and returned to 100% Methanol.

From glycerol, BABB, or Methanol, embryos were transferred into a 100% Ethanol solution. If the embryos were stored in glycerol, they were first washed a few times in TTW to remove the glycerol before transferring to the 100% Ethanol solution. If the embryos were in BABB, they were first washed a few times in Ethanol to remove the BABB before transferring to the 100% Ethanol solution. If the embryos were in Methanol, they were transferred directly to the 100% Ethanol solution. The Ethanol was decanted from the dehydrated embryos and exchanged for Xylene. The embryos were incubated twice for 5 minutes each time in Xylene. Then the Xylene was removed and replaced with molten paraplast. The embryos were incubated twice for 30-60 minutes each time in the molten paraplast. Finally, the embryos were mounted in fresh paraplast.

Figure 4:
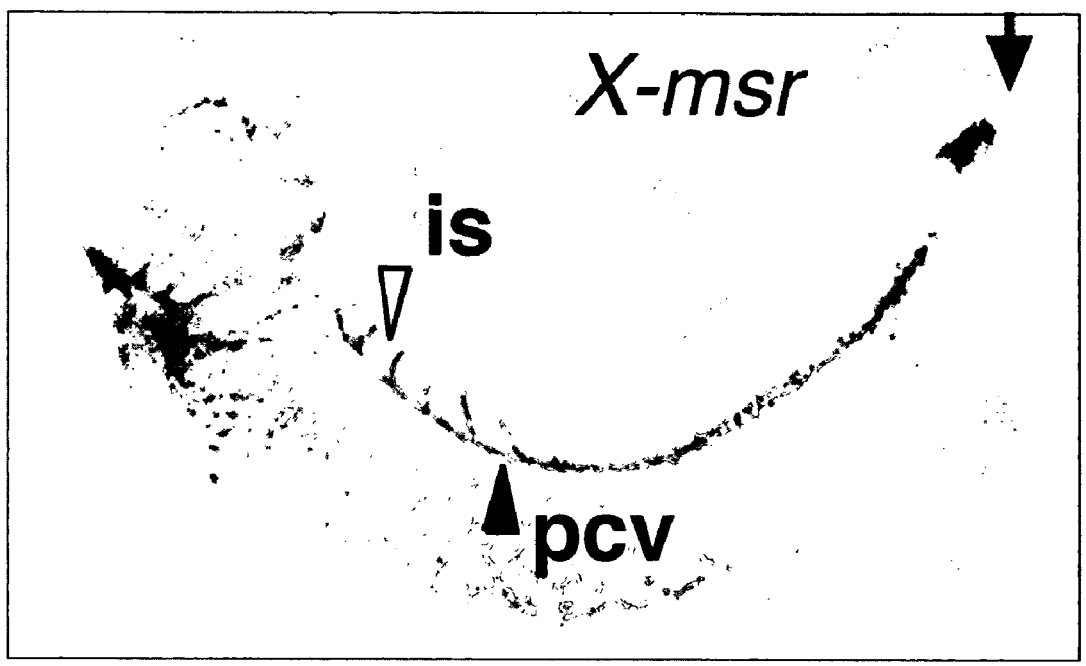
FIG. 4 is a photomicrograph of a frog embryo in which APJ transcripts were detected using an in situ hybridization protocol. These data reveal that APJ is strongly expressed in the developing vasculature. The "is" denotes intersomitic vessel, and the posterior cardinal vein is denoted "pcv" in this figure. APJ is also known as "X-msr" in *Xenopus*, as is indicated in this figure.
Figure 5:
FIG. 5 is a photomicrograph of an in situ hybridization of a frog embryo probed with either (A) apelin antisense sequences or (B) APJ antisense sequences. These data show that both apelin and APJ are expressed in the developing blood vessels, especially the growing intersomitic vessels. Panel A shows the expression of apelin, and panel B shows the expression of APJ.
Figure 5:

FIGS. 4 and 5 show the results of in situ hybridization experiments staining for apelin and APJ. These data demonstrate that apelin and APJ are both expressed in the developing vasculature.

Example 3

Analysis of the Effect of Apelin on Vascular Growth

Effect of Apelin-Soaked Beads

The apelin 13-mer C-terminal peptide (SEQ ID NO:4), which shows 100% sequence identity between human and frog, was synthesized to greater than 90% purity by Sigma-Genosys. The N-terminal glutamine was modified to a pyro-glutamic acid residue to avoid cyclization and poor yield during the manufacturing process. A mutant control apelin peptide was also prepared in which the last four residues were substituted with alanine residues.

AFFI-GEL blue beads (Bio-Rad, 50-75 µm diameter) were soaked in a solution of apelin peptide (0.1 mg/ml), mutated apelin peptide (0.25 mg/ml), BSA (Sigma, 1 mg/ml), or rm VEGF-164 (R&D Systems, 0.25 mg/ml) for 1 hour on ice. Beads were microsurgically implanted in an avascular region, the posterior lateral mesoderm, of stage 24-26 embryos. Embryos were cultured in 0.2×MMR until stage 35-37, at which time they were prepared for whole mount in situ hybridization analysis as described in Example 2. The embryonic vascular system was visualized using an antisense probe directed against transcripts encoding the *Xenopus* vascular marker, erg (Baltzinger et al., 1999, Dev. Dyn. 216:420-33).

Figure 6:
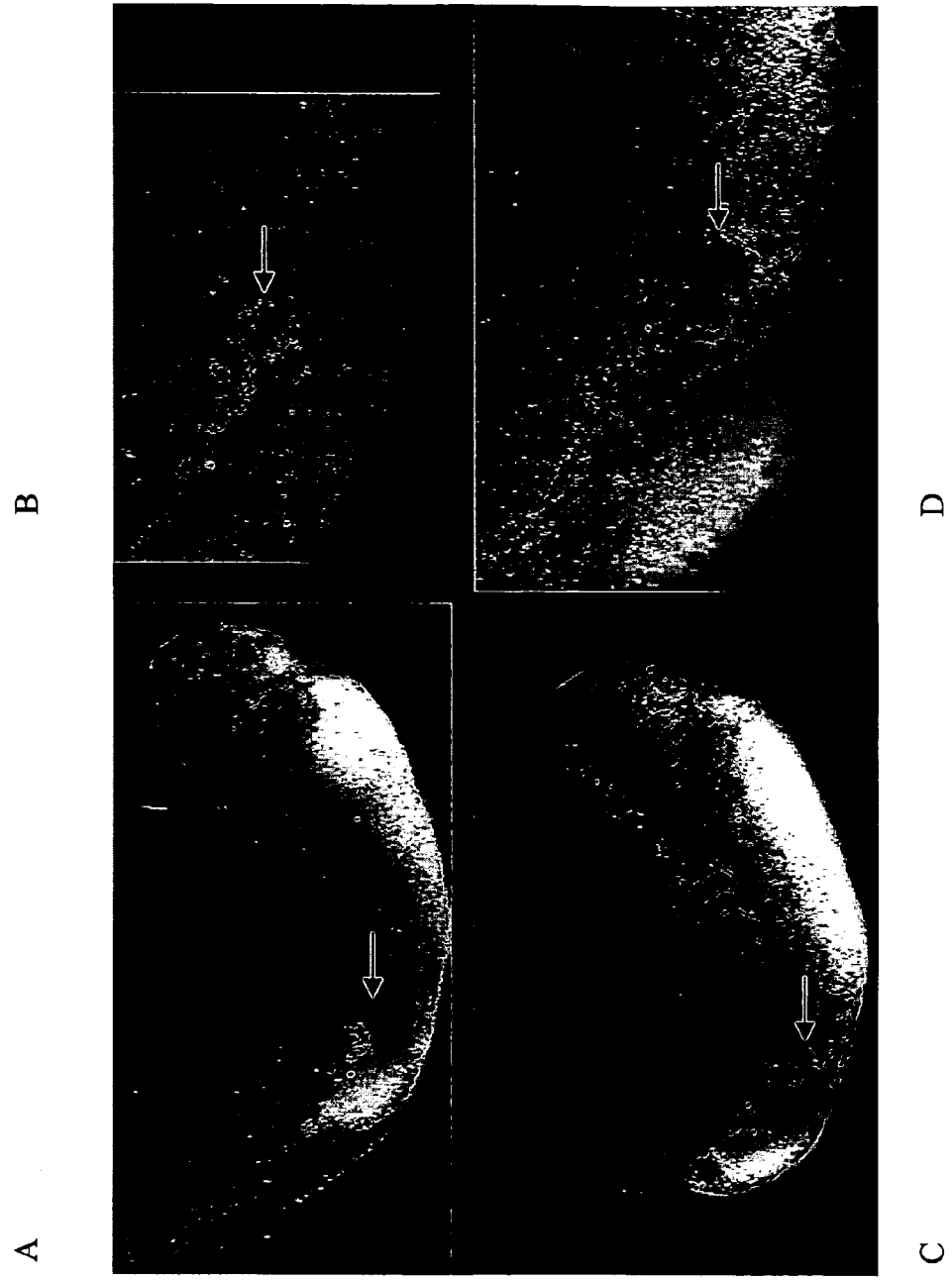
FIG. 6 is a photomicrograph of an in situ hybridization of a frog embryo stained with a vascular marker to visualize blood vessels, showing outgrowth of the vasculature toward the apelin-soaked beads. In this case, the probe detects transcripts for the vascular transcription factor erg. Beads soaked in the thirteen amino acid apelin peptide were implanted into frog embryos and are indicated here by the arrows. Panel A and B show different magnifications of the same embryo at A) 50× and B) 150×. Panel C and D show different magnifications of the same embryo at C) 50× and D) 150×.

The photomicrographs of the in situ hybridization show that there is outgrowth of developing blood vessels toward the apelin-soaked beads (FIG. 6). The photomicrographs of the in situ hybridization using VEGF-soaked beads show that there is a nearly identical outgrowth of developing blood vessels as was shown with the apelin-soaked beads (data not shown). Beads containing only the mutated apelin peptide or BSA produced no visible effects of BSA or the mutated apelin peptide on vascular outgrowth (data not shown).

Chick Chorioallantoic Membrane (CAM) Assay

Figure 7:
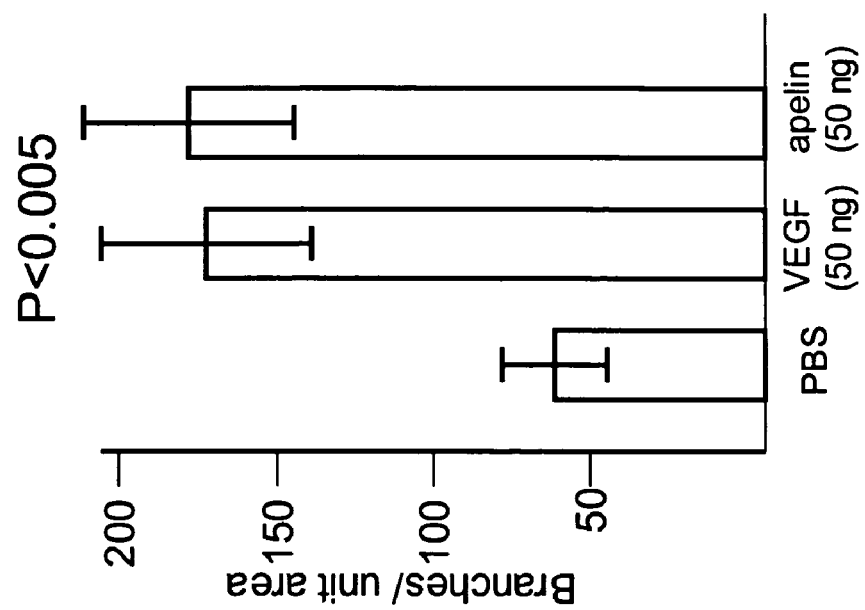
FIG. 7 shows the results of chicken chorioallantoic membrane (CAM) assays. Panels A and B are photomicrographs of blood vessels that formed in association with membranes that had been treated with A) PBS buffer or B) 50 ng apelin-13. Panel C is a graph showing the quantitation of results from duplicate CAM assays (units are branches/unit area). The membranes had been treated with PBS buffer, 50 ng VEGF, or 50 ng apelin-13, as indicated. Panel B demonstrates that apelin results in an increase in blood vessel formation, as well as an increase in leakage from the blood vessels. These results indicate that apelin has an effect similar to that of VEGF, as an angiogenic factor and/or as a vascular permeability factor, as assayed using the chicken CAM procedure.
Figure 7:
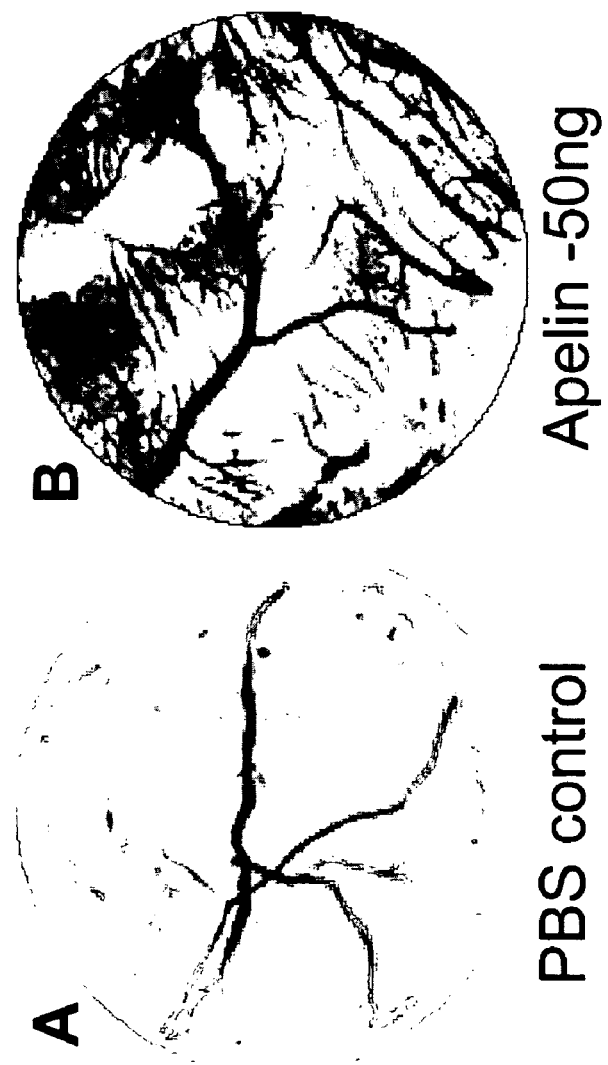

Chicken eggs were incubated at 37° C. in a humidified chamber. On day 10 of development, a small window was made in the outer shell of the egg, and the CAM was released from its attachment to the inner shell membrane. A larger window was then made in the egg to allow for addition of the filter paper containing growth factor. Filter discs (3MM Whatman) of 7-8 mm diameter were pretreated with 10 µl of 0.1% cortisone acetate (Sigma) solution to avoid inflammation of the CAM. The filter discs were air dried prior to application of growth factors. Then 50 ng of apelin-13 or VEGF in 10 µl volume was absorbed into the filter discs; 10 µl of PBS absorbed to the discs was used as a negative control. After air-drying, the filter discs were placed on the CAM, and eggs were returned to the incubator for three days. Filter discs and the attached CAM were then excised, washed with PBS, trimmed to the size of the disc, and photographed for quantitative analysis (FIGS. 7A and 7B). The number of vessel branch points was determined using a blind protocol. The results are shown as the mean of three independent experiments +/−s.e.m. (FIG. 7C).

These data show that blood vessel formation and leakage of blood vessels both increased in the CAM exposed to apelin-13 (FIG. 7B), as compared to the CAM exposed to the control PBS (FIG. 7A), demonstrating the angiogenic effect of apelin-13 in this assay. It is notable that apelin demonstrated a very similar effect to VEGF, as an angiogenic factor and/or as a vascular permeability factor, based on the results of this CAM assay.

Example 4

Effect of Apelin on Vascular Proliferation and Migration

Bovine aortic endothelial cells (BAE) were cultured in DMEM supplemented with 10% fetal bovine serum (FBS) and penicillin/streptomycin. For generation of stable cell lines expressing APJ, the mouse APJ coding region was cloned into the pcDNA 3.1 vector downstream of the CMV promoter, in frame with a myc epitope at the C-terminal end of the protein, and upstream of the neomycin gene. Bovine aortic endothelial (BAE) cells were transfected with this construction using the SUPERFECT transfection kit (Qiagen) and selected for resistance to G418 (600 µg/ml). Colonies were isolated and screened using RT-PCR for expression of mouse APJ and also by immunocytochemistry for expression of the myc epitope. A total of 14 clones were found to express mouse APJ, and one of these (BAE/APJ#2) was used for both the proliferation and migration assays.

BAE/APJ#2 cells plated at 70% confluence in 8 well culture slides (VWR) were serum starved for 48 hours and then stimulated with apelin (10 ng/ml), VEGF (10 ng/ml) or FGF-2 (10 ng/ml) in DMEM, or DMEM alone, for 24 hours. Proliferation inhibition experiments were carried out using the VEGF pathway inhibitor SU1498 (Sigma) which blocks phosphorylation of the VEGFR2 receptor. SU1498 was included in proliferation cultures at a concentration of 10 ng/ml and results were assayed using BrdU incorporation. After growth factor incubation, BrdU was added to each well at a final concentration of 10 µM for 2 hours, cells were washed, and fixed for BrdU immunocytochemistry.

Figure 8:
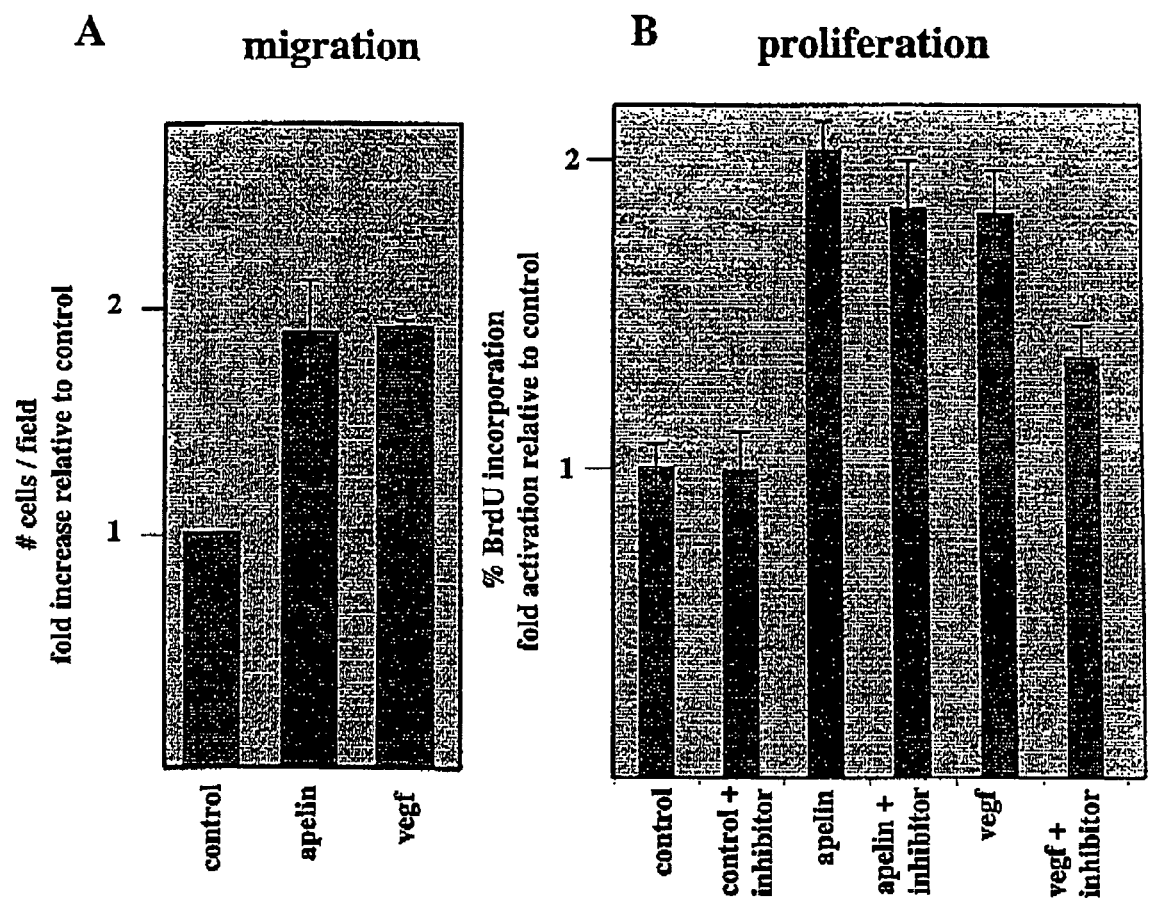
FIG. 8A is a graph showing the increase in migration of bovine aortic endothelial (BAE) cells in response to 10 ng/ml apelin or VEGF. The blood vessel migration is measured by the number of cells per field. A total of four fields were counted for each membrane, and the experiments were performed in triplicate +/−s.e.m.
FIG. 8B is a graph showing the proliferation of bovine aortic endothelial (BAE) cells in response to VEGF or apelin, in the presence or absence of the VEGF pathway inhibitor SU1498. The results shown are the mean of triplicate experiments +/−the s.e.m. These data show that the VEGF pathway inhibitor SU1498 partially inhibits VEGF-mediated proliferation, but has no significant effect on apelin-mediated proliferation.

Cells were fixed in 100% ice cold methanol at 4° C. for 2 hours to overnight. Prior to staining, cells were air dried and rehydrated for 3 minutes with PBS buffer. DNA was denatured at 37° C. with 2 M HCl, and neutralized with 2 washes for 5 minutes in 0.1 M borate buffer (pH 8.5). Cells were washed 3 times for 5 minutes each with PBS and blocked for 30 minutes in 1% normal goat serum/2% BSA. FITC-labeled anti-BrdU antibody (5 µg/ml) in block was added for 1 hour at room temperature. Cells were counterstained with propidium iodide following several washes in PBS buffer. For each experiment, 4 random fields were photographed for determination of percentage BrdU labeling. The results presented in FIG. 8B are the mean of 3 independent experiments, +/−S.E.M. These data demonstrate that apelin promotes endothelial cell proliferation to a similar extent as VEGF, and suggest that VEGF and apelin initiate this proliferation through a different pathway, as apelin was still able to promote proliferation in the presence of the VEGF inhibitor.

Cell migration assays were performed using Transwell cell culture migration chambers (Becton Dickinson) with 8 micron pore size. BAE/APJ#2 cells were plated in serum free conditions in 100 µl at a concentration of $1 \times 10^5$ ml in the upper chamber of the migration chamber. Following cell attachment to the membrane, 10 ng/ml of growth factor was added to the bottom chamber, in a total volume of 0.5 ml. Cells were stimulated with growth factor in DMEM for 16 hours, or DMEM alone, at which time the cells remaining in the upper chamber were removed using a cotton tip applicator. Following a brief wash with PBS the remaining cells were fixed in 3.7% formaldehyde at 4° C. for 1 hour. Cells attached to the membrane in the lower chamber were stained with DAPI, and 3 random fields were counted for each experimental condition. The results presented in FIG. 8A are the mean of 3 independent experiments, +/−S.E.M. These data demonstrate that apelin promotes endothelial cell migration.

Example 5

Effect of Antisense Nucleic Acids on Vascular Growth

Figure 9:
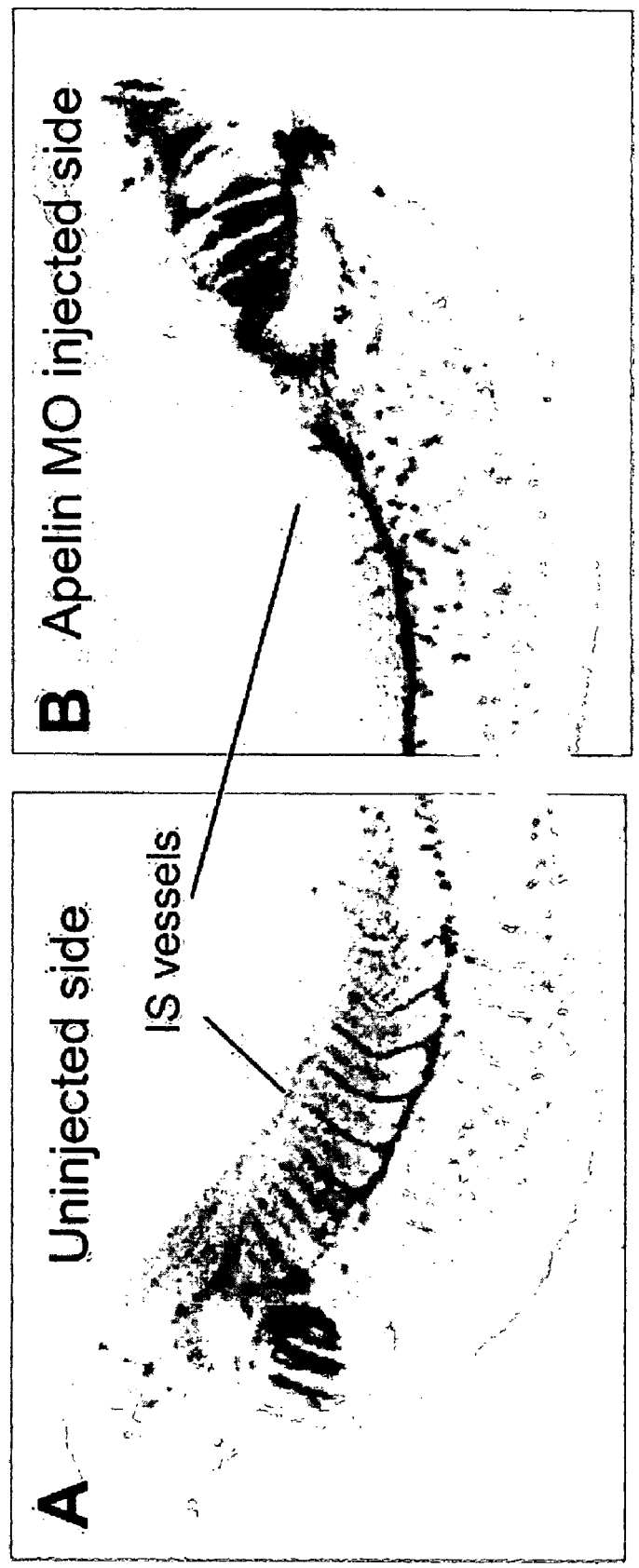
FIG. 9 is photomicrograph of an in situ hybridization of a frog embryo stained to detect transcripts of the vascular marker erg, to visualize developing blood vessels. Panel A shows the uninjected side of the frog embryo. Panel B shows the side of the frog embryo that was injected with the ap1 apelin antisense morpholino. These data show that a reduction in apelin protein in the embryo causes a disruption in vascular growth.

Loss-of-function experiments were performed using antisense morpholino oligonucleotides (MOs) (Gene Tools, Philomath, Oreg.), and the results are shown in FIG. 9. All morpholino oligonucleotides were designed based on recommendations from Gene Tools. Two distinct antisense oligonucleotides overlapping the initiation ATG were designed to block translation from both *Xenopus laevis* pseudoallelic copies of the apelin transcript.

The primers used were as follows:

```
ap1  5'-GTGCCCAAAGTCTGAGATTCATGTT-3'   (SEQ ID NO:
                                        6)
and ap2  5'-GATTCATGTTTCTTGTGGCTGAGTG-3'.  (SEQ ID NO:
                                        7)
```

A 5 base pair mismatch control morpholino oligonucleotide (ap2 mm) was designed for the ap2 morpholino oligonucleotide: ap2 mm 5'-GATTgATcTTTgTTGTGcCTcAGTG-3' (SEQ ID NO:8); the mismatch bases are represented in lowercase type.

One antisense morpholino oligonucleotide, designed to block translation from both copies of the APJ transcript, was targeted immediately upstream of the initiation ATG: apj 5'-AAGGCTGTGTGGAAGCAATAGAAAG-3' (SEQ ID NO:9).

The 5 base pair mismatch control sequence for the apj morpholino oligonucleotide (apjmm) is: apjmm 5'-AAGcCTcTGTGcAAcCAATAcAAAG-3' (SEQ ID NO:10); the mismatch bases indicated in lowercase.

Morpholino oligonucleotides were reconstituted in 50 mM HEPES buffer (pH 8.0) and injected into the frog embryo. The ap1 MO was injected at 15 ng per embryo, and the ap2 and apj MOs were injected at 7.5 ng. Mismatch controls, ap2 mm and apjmm, were used at twice the experimental dose (15 ng). The MOs were injected into one cell of a 2 cell embryo together with Texas Red Dextran (10 ng; Molecular Probes) as a lineage tracer. Embryos were grown to stage 35 when they were assayed by in situ hybridization using the vascular marker, erg.

The ap1 morpholino injections resulted in an inhibition of angiogenic growth of embryonic blood vessels in 67% of the embryos (N=76)(FIG. 9B). This decrease in vascularization was clearly evidenced by the lack of the intersomitic vessels which develop by an angiogenic mechanism. The ap2 morpholino, which overlaps the sequence of the ap1 morpholino, was used to confirm the effect of apelin on angiogenic growth in the embryos. Using half the concentration (7.5 ng), the ap2 morpholino still resulted in the loss of intersomitic vessel formation in 63% of the embryos (N=64)(data not shown). Similarly, 7.5 ng of an antisense morpholino to the APJ receptor resulted in a decrease in angiogenic growth of blood vessels in 71% of the embryos (N=48)(data not shown). By contrast, 15 ng of either the ap2 mm or apjmm mismatch control morpholinos did not produce a detectable alteration in the vascular growth of the embryos (data not shown). These data clearly demonstrate that inhibition of apelin results in an inhibition of angiogenic growth of embryonic blood vessels.

Example 6

Apelin Expression in Human Tumors

Figure 10:
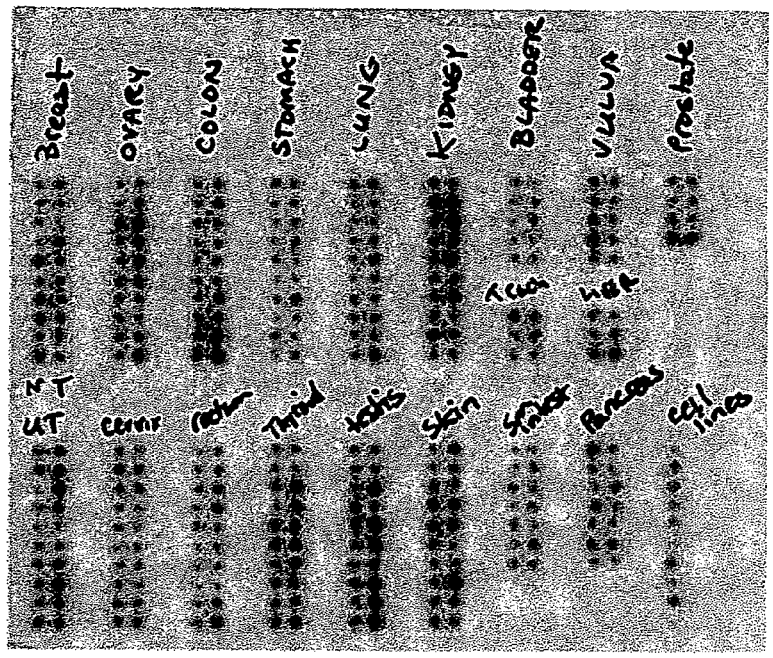
FIG. 10 shows expression of apelin mRNA in a significant portion of human tumors. The membrane (BD Biosciences, San Jose, Calif., cat. # 7847-1) contained cDNA from 154 human tumors of different tissues, as well as a control sample corresponding to each of the tumor samples that was from non-tumor adjacent tissue from the same individual.
Figure 10:
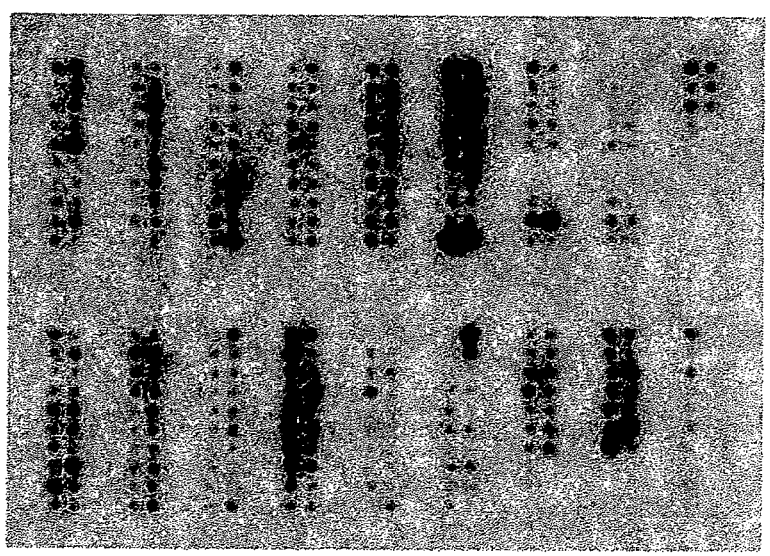

A dot blot membrane carrying cDNA prepared from 154 human tumors was obtained from BD Biosciences (San Jose, Calif.). Each tumor sample was accompanied by an adjacent non-tumor tissue from the same individual. An approximately 2 kb fragment of the human apelin sequence was labeled with $^{32}$P by the Random Priming method, using a standard protocol (Feinberg and Vogelstein, 1984). The $^{32}$P-labeled probe was hybridized overnight with the dot blot membrane in a hybridization solution provided by BD with the membrane (BD EXPRESSHYB Hybridization solution). After hybridization, the membrane was washed with prewarmed Wash Solution I (2×SSC, 0.5% SDS) for 30 minutes at 68° C., followed by two additional washes for 30 minutes each in Wash Solution I at 68° C. The membrane was then washed two times in prewarmed Wash Solution II (0.2×SSC, 0.5% SDS) for 30 minutes each at 68° C. The membrane was then wrapped in plastic wrap and exposed to X-ray film, in the presence of an intensifying screen at 80° C. for 17 hours. Apelin expression was increased in approximately one third of the 154 tumor samples, relative to adjacent non-tumor tissue (58 out of 154 samples) (FIG. 10A).

The apelin probe was stripped from the membrane by washing in a boiling 0.5% SDS solution for 30-40 minutes. Then the membrane was screened with a $^{32}$P-labeled probe for human VEGF-A (approximately 700 base fragment), a positive control for expression of a known angiogenic agent. Hybridization and washing conditions were the same as with the apelin probe. VEGF mRNA expression also was upregulated in approximately one third of the human tumor samples, relative to the non-tumor tissue sample controls (54 out of 154 samples)(FIG. 10B).

Similar results were obtained with a second membrane obtained from BD Biosciences (carrying the cDNA prepared from the 154 human tumors and non-tumor tissue controls) that was probed first with the $^{32}$P-labeled apelin probe, then stripped and probed with the $^{32}$P-labeled VEGF-A probe (data not shown). These data demonstrate that the expression of apelin is upregulated in a significant portion of human tumors, relative to non-tumor tissue, consistent with a role for apelin in promotion of tumorigenesis.

Example 7

Hypoxia-Induced Regulation of Apelin Expression

Under hypoxic conditions, the expression of various genes is regulated by a transcription factor denoted Hypoxia-Induced Factor-1alpha (HIF-1). During tumor growth, it is likely that there are periods of hypoxia which act to stimulate new blood vessel growth. Because apelin has been shown here to be involved in promoting angiogenesis, the sequence of the human, mouse, and zebrafish apelin genes and their surrounding sequences were analyzed to determine if apelin expression may be regulated by HIF-1α. The consensus sequence for an HIF-1α recognition site is BACGTGK (SEQ ID NO:11). In this consensus sequence the B denotes a C, G, or T nucleotide, but not an A nucleotide; the K denotes a G or T nucleotide.

Figure 11:
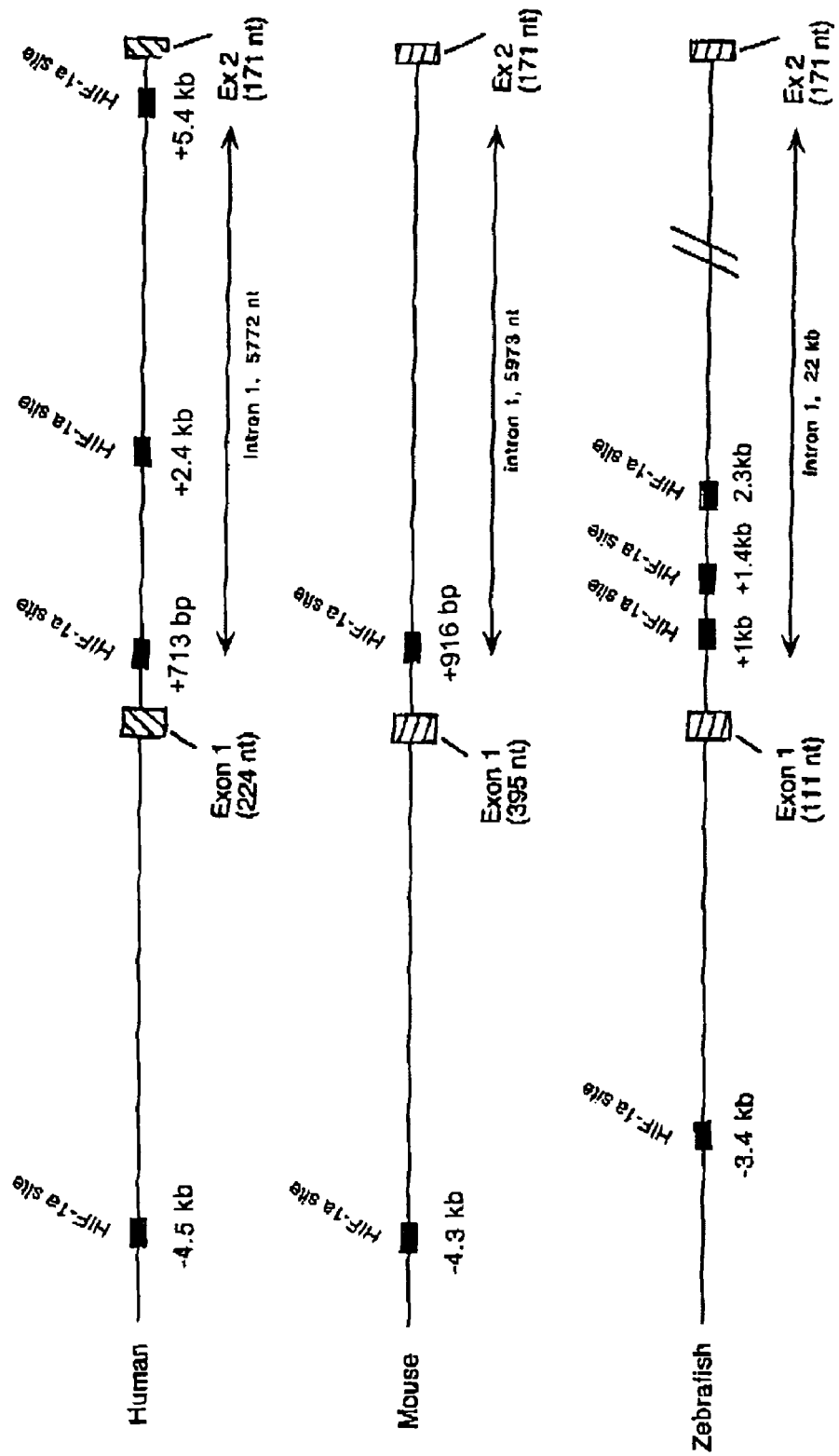
FIG. 11 is a schematic representation of the regulatory region of the human, mouse, and zebrafish apelin genes, depicting the putative HIF-1α recognition sequences.

FIG. 11 shows that two to four HIF-1α recognition sites were present in the apelin regulatory regions. All sites mapped had a confidence value of 0.88 or greater, according to VISTA transcription factor binding site analysis software. The human apelin regions contained an HIF-1α site (GAGACGTGGA (SEQ ID NO:12); VISTA confidence value=0.899) located at −4.5 kb (4.5 kb upstream from the transcription initiation site) and three sites within intron 1 (located at approximately +713 bp, +2.4 kb, and +5.4 kb downstream of the transcription initiation site). The relative sequences and confidence values of these three sites are CAGACGTGACA (SEQ ID NO: 13; VISTA confidence value=0.964), TGTACGTGG (SEQ ID NO: 14; VISTA confidence value=0.964), and AATGACGTGATG (SEQ ID NO:15; VISTA confidence value=0.916), respectively.

Similarly, the mouse apelin regulatory region contains two HIF-1α recognition sites at −4.3 kb and +916 bp with respect to the transcription initiation site. The zebrafish regulatory region contains four HIF-1α recognition sites at approximately −3.4 kb, +1 kb, +1.4 kb, and +2.3 kb with respect to the transcription initiation site.

The VEGF-A gene also has been shown to contain two HIF-1α consensus sites, however, only the site at approximately −975 bp (TACGTGGG (SEQ ID NO: 16) is required for the hypoxia response. Therefore, it is possible that one or more of the consensus sequences in the apelin regulatory region may not be necessary for a hypoxia response.

Because HIF-1α consensus sites are present in the apelin regulatory region, experiments were conducted to determine whether apelin expression is hypoxia responsive and regulated by HIF-1α. Upregulation of apelin expression under hypoxic conditions would be consistent with a role for apelin in promotion of tumor angiogenesis. Preliminary experiments were carried out using primary rat cardiomyocyte cells in culture and treatment with cobalt chloride. This procedure is accepted as an equivalent to culturing cells under hypoxic conditions because HIF-1α is a metal responsive transcription protein (Ladoux and Frelin, 1994; Piret et al., 2002; Maxwell and Salnikow, 2004). Fetal rat cardiac myocytes were plated and cultured in DMEM (Invitrogen, Carlsbad, Calif.) supplemented with 10% fetal calf serum and penicillin/streptomyocin at 37° C. After four days of culture, medium was removed, and cells were treated with fresh media containing 150 μM Cobalt Chloride (Piret et al., 2002). Control cells were treated with fresh media that did not contain Cobalt Chloride. After 4 hours of culture, cells were harvested, and total RNA was extracted using the Trizol procedure according to the manufacturers recommendations (Invitrogen, Carlsbad, Calif.).

Figure 12:
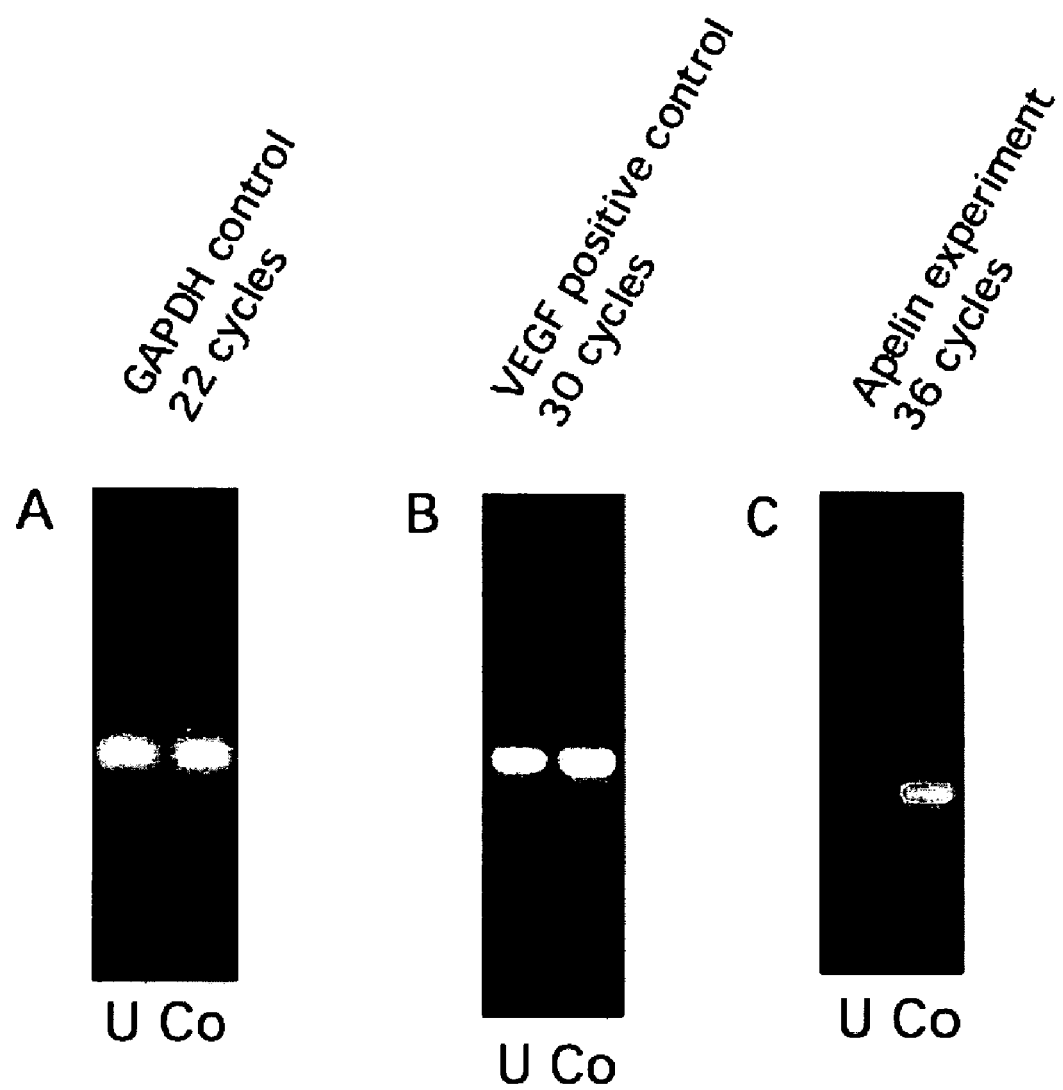
FIG. 12 shows photographs of electrophoretic gels, demonstrating the effect of conditions that mimic hypoxia on gene expression. Primary rat cardiomyocyte cells were cultured in DMEM (Invitrogen, Carlsbad, Calif.) supplemented with 10% fetal calf serum and penicillin/streptomycin at 37° C.

Following preparation of cDNA using standard procedures, the Cobalt Chloride treated or untreated samples were assayed for transcript levels using polymerase chain reaction (PCR) and sequence specific primers for GAPDH as a normalization control, vascular endothelial growth factor (VEGF) as a positive control, or apelin. Following PCR, amplification products were fractionated on an agarose gel and visualized using ethidium bromide staining under ultraviolet light (FIG. 12). GADPH expression was assayed a standardization control for template concentration, and VEGF expression was assayed as a positive control known to respond to hypoxic conditions. As shown in FIG. 12C, apelin expression was significantly increased in response to these conditions that mimic hypoxia. This upregulation of apelin under these conditions strongly suggest that apelin plays a role in tumor angiogenesis.

APPENDIX

```
Amino Acid Sequence of Preproapelin
from Homo sapiens
MNLRLCVQALLLLWLSLTAVCGGSLMPLPDGNGLED    (SEQ ID NO: 1)

GNVRHLVQPRGSRNGPGPWQGGRRKFRRQRPRLSHK

GPMPF

Amino Acid Sequence of Apelin-36
from Homo sapiens
LVQPRGSRNGPGPWQGGRRKFRRQRPRLSHKGPMPF    (SEQ ID NO: 2)

Amino Acid Sequence of Apelin-17
from Homo sapiens
KFRRQRPRLSHKGPMPF                       (SEQ ID NO: 3)

Amino Acid Sequence of Apelin-13
QRPRLSHKGPMPF                           (SEQ ID NO: 4)

Amino Acid Sequence of Apelin-13
from Zebrafish
PRPRLSHKGPMPF                           (SEQ ID NO: 5)

Amino Acid Sequence of APJ receptor
from Homo sapiens
MEEGGDFDNYYGADNQSECEYTDWKSSGALIPAIYM    (SEQ ID NO: 17)

LVFLLGTTGNGLVLWTVFRSSREKRRSADIFIASLA

VADLTFVVTLPLWATYTYRDYDWPFGTFFCKLSSYL

IFVNMYASVFCLTGLSFDRYLAIVRPVANARLRLRV

SGAVATAVLWVLAALLAMPVMVLRTTGDLENTTKVQ

CYMDYSMVATVSSEWAWEVGLGVSSTTVGFVVPFTI

MLTCYFFIAQTIAGHFRKERIEGLRKRRRLLSIIVV

LVVTFALCWMPYHLVKTLYMLGSLLHWPCDFDLFLM

NIFPYCTCISYVNSCLNPFLYAFFDPRFRQACTSML

CCGQSRCAGTSHSSSGEKSASYSSGHSQGPGPNMGK

GGEQMHEKSIPYSQETLVVD
```

---

I claim:

1. A method of inhibiting angiogenesis in a patient in need thereof, comprising
administering to the patient an angiogenesis-inhibiting amount of a composition comprising an anti-apelin antibody or fragment thereof that binds apelin polypeptide of SEQ ID NO:4 and inhibits angiogenesis, wherein the angiogenesis is characterized by in vivo generation of a new blood vessel from an existing blood vessel.

2. The method of claim 1, wherein the composition further comprises an anti-cancer agent and wherein the anti-cancer agent is selected from the group consisting of a chemotherapeutic agent, a radiotherapeutic agent, an anti-angiogenesis agent, and an apoptosis-inducing agent.

3. The method of claim 2, wherein the composition comprises an anti-angiogenesis agent that inhibits an angiogenic factor selected from the group consisting of VEGF (VEGF-A), VEGF-B, VEGF-C, VEGF-D, VEGF-E, PIGF, acidic fibroblast growth factor (FGF-1), basic fibroblast growth factor (FGF-2), PDGFB, EGF, LPA, HGF, PD-ECF, IL-8, angiogenin, TNF-alpha, TGF-beta, TGF-alpha, proliferin, and PLGF.

4. The method of claim 1, wherein the composition comprises a pharmaceutically acceptable carrier.

5. The method of claim 1, wherein the patient is a mammal.

6. The method of claim 1, wherein the patient is a human.

7. The method of claim 1, wherein the patient has a disease or condition involving angiogenesis.

8. The method of claim 7, further comprising administering to the patient a therapeutically effective amount of an anti-cancer agent, wherein the anti-cancer agent is selected from the group consisting of a chemotherapeutic agent, a radiotherapeutic agent, an anti-angiogenic agent, and an apoptosis-inducing agent.

9. The method of claim 8, wherein the anti-cancer agent is an anti-angiogenic agent.

10. The method of claim 8, wherein the anti-angiogenic agent is an inhibitor of an angiogenic factor selected from the group consisting of VEGF (VEGF-A), VEGF-B, VEGF-C, VEGF-D, VEGF-E, PIGF, acidic fibroblast growth factor (FGF-1), basic fibroblast growth factor (FGF-2), PDGFB, EGF, LPA, HGF, PD-ECF, IL-8, angiogenin, TNF-alpha, TGF-beta, TGF-alpha, proliferin, and PLGF.

11. A method of inhibiting angiogenesis in a biological sample comprising contacting the biological sample with an angiogenesis-inhibiting amount of a composition comprising an anti-apelin antibody or fragment thereof that binds the apelin polypeptide of SEQ ID NO:4 and inhibits angiogenesis, wherein the angiogenesis is characterized by in vivo generation of a new blood vessel from an existing blood vessel.

12. The method of claim 11, wherein the biological sample is a mammalian biological sample.

13. The method of claim 11, wherein the biological sample is a human biological sample.

* * * * *

SEQUENCE LISTING

<160> NUMBER OF SEQ ID NOS: 21

<210> SEQ ID NO 1
<211> LENGTH: 77
<212> TYPE: PRT
<213> ORGANISM: Homo sapiens

<400> SEQUENCE: 1

Met Asn Leu Arg Leu Cys Val Gln Ala Leu Leu Leu Leu Trp Leu Ser
 1               5                  10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

```
Arg Asn Gly Pro Gly Pro Trp Gln Gly Gly Arg Lys Phe Arg Arg
     50                  55                  60

Gln Arg Pro Arg Leu Ser His Lys Gly Pro Met Pro Phe
 65                  70                  75

<210> SEQ ID NO 2
<211> LENGTH: 36
<212> TYPE: PRT
<213> ORGANISM: Homo sapiens

<400> SEQUENCE: 2

Leu Val Gln Pro Arg Gly Ser Arg Asn Gly Pro Gly Pro Trp Gln Gly
 1               5                  10                  15

Gly Arg Arg Lys Phe Arg Arg Gln Arg Pro Arg Leu Ser His Lys Gly
             20                  25                  30

Pro Met Pro Phe
         35

<210> SEQ ID NO 3
<211> LENGTH: 17
<212> TYPE: PRT
<213> ORGANISM: Homo sapiens

<400> SEQUENCE: 3

Lys Phe Arg Arg Gln Arg Pro Arg Leu Ser His Lys Gly Pro Met Pro
 1               5                  10                  15

Phe

<210> SEQ ID NO 4
<211> LENGTH: 13
<212> TYPE: PRT
<213> ORGANISM: Homo sapiens

<400> SEQUENCE: 4

Gln Arg Pro Arg Leu Ser His Lys Gly Pro Met Pro Phe
 1               5                  10

<210> SEQ ID NO 5
<211> LENGTH: 13
<212> TYPE: PRT
<213> ORGANISM: Brachydanio rerio

<400> SEQUENCE: 5

Pro Arg Pro Arg Leu Ser His Lys Gly Pro Met Pro Phe
 1               5                  10

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcccaaag tctgagattc atgtt                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
gattcatgtt tcttgtggct gagtg                                            25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gattgatctt tgttgtgcct cagtg                                            25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaggctgtgt ggaagcaata gaaag                                            25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aagcctctgt gcaaccaata caaag                                            25

<210> SEQ ID NO 11
<211> LENGTH: 7
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 11 bacgtgk                                                                 7

<210> SEQ ID NO 12
<211> LENGTH: 10
<212> TYPE: DNA
<213> ORGANISM: Homo sapiens

<400> SEQUENCE: 12
gagacgtgga                                                             10

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagacgtgac a                                                           11
```

-continued

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 tgtacgtgg                                                              9

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatgacgtga tg                                                         12

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 tacgtggg                                                               8

<210> SEQ ID NO 17
<211> LENGTH: 380
<212> TYPE: PRT
<213> ORGANISM: Homo sapiens

<400> SEQUENCE: 17

Met Glu Glu Gly Gly Asp Phe Asp Asn Tyr Tyr Gly Ala Asp Asn Gln
 1               5                  10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

```
Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
            195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
            275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
            355                 360                 365

Ser Ile Pro Tyr Ser Gln Glu Thr Leu Val Val Asp
            370                 375                 380

<210> SEQ ID NO 18
<211> LENGTH: 14
<212> TYPE: PRT
<213> ORGANISM: Rana sp.

<400> SEQUENCE: 18

Arg Gln Arg Pro Arg Leu Ser His Lys Gly Pro Met Pro Phe
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 19

Arg Gln Arg Pro Arg Leu Ser His Lys Gly Pro Met Pro Phe
 1               5                  10

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Lys Lys Arg
 1
```

```
-continued
<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Arg Arg
  1
```